United States Patent [19]

Cox et al.

[11] Patent Number: 5,216,126
[45] Date of Patent: Jun. 1, 1993

[54] RECEPTOR POLYPEPTIDES AND THEIR PRODUCTION AND USES

[75] Inventors: Edward T. Cox, Foster City; Jennie P. Mather, Millbrae; Mary B. Sliwkowski, San Carlos; Teresa K. Woodruff, Millbrae, all of Calif.

[73] Assignee: Genentech, Inc., South San Francisco, Calif.

[21] Appl. No.: 716,826

[22] Filed: Jun. 19, 1991

[51] Int. Cl.$^5$ .............. C07K 15/00; A61K 37/43; A61K 39/00; A61K 35/10
[52] U.S. Cl. ......................... 530/350; 514/8; 530/388.22; 530/389.1
[58] Field of Search ............... 530/350, 387, 388.22, 530/389.1; 514/8

[56] References Cited

FOREIGN PATENT DOCUMENTS 0369861  5/1990  European Pat. Off.

OTHER PUBLICATIONS

Current Protocols in Molecular Biology John Wiley & Sons 1987 Chapter 11.
Cheifetz et al., J. Biol. Chem., 263:17225–17228 (1988).
Sporn & Roberts, Nature, 313:745–747 (1985).
Keller et al., J. Cell. Biochem., 39:175–184 (1989).
Kimchi et al., Science, 240:196–199 (1988).
Kehrl et al., J. Immunol., 143:1868–1874 (1989).
Segarini et al., Mol. Endocr., 3:261–272 (1989).
Jennings et al., J. Cell. Physiol., 137:167–172 (1988).
Chiefetz et al., J. Biol. Chem., 263:10783–10789 (1988).
Segarini & Seyedin, J. Biol. Chem., 263:8366–8370 (1988).
Cheifetz et al., J. Biol. Chem., 261:9972–9978 (1986).
Massague, J. Biol. Chem., 260:7059–7066 (1985).
Massague & Like, J. Biol. Chem., 260:2636–2645 (1985).
Tucker et al., PNAS USA, 81:6757–6761 (1984).
Frolik et al., J. Biol. Chem., 259:10995–11000 (1984).
Cheifetz et al., J. Biol-Chem., 263:16984–16991 (1988).
Segarini et al., J. Biol. Chem., 262:14655–14662 (1987).
Cheifetz et al., Cell, 48:409–415 (1987).
Mathews & Vale, Cell, 65:973–982 (1991).
Wakefield et al., J. Cell Biol., 105:965–975 (1987).
Georgi et al., Cell, 61(3):635–645 (1990).

*Primary Examiner*—Y. Christina Chan
*Assistant Examiner*—Donald E. Adams
*Attorney, Agent, or Firm*—Janet E. Hasak

[57] ABSTRACT

An isolated TGF-$\beta$ supergene family (TSF) receptor polypeptide is provided. This polypeptide preferably is an inhibin/activin receptor polypeptide and has at least 75% sequence identity with the mature human inhibin-/activin receptor sequence. Also provided is a method for purifying TGF-$\beta$ supergene family members such as inhibin or activin using the polypeptide, and a method for screening for compounds with TGF-$\beta$ supergene family member activity by contacting the compound with the polypeptide and detecting if binding has occurred and the compound is active.

4 Claims, 4 Drawing Sheets

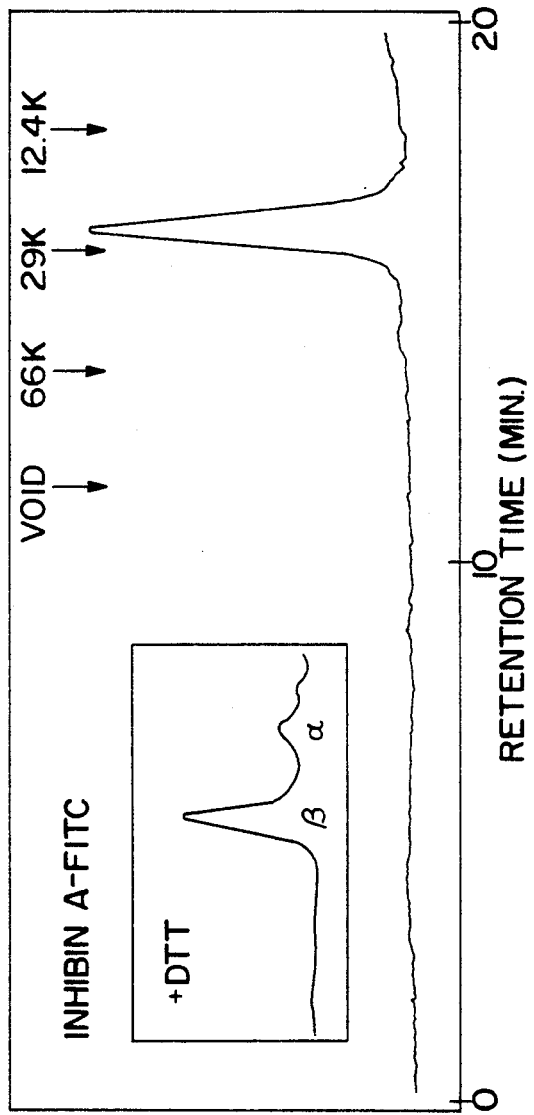
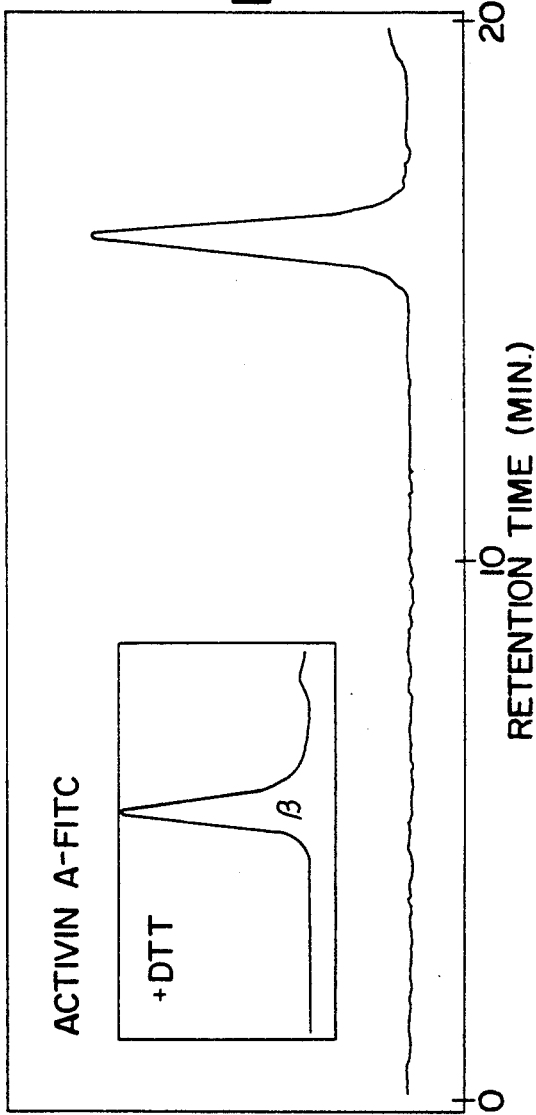

TM4 -cAMP

TM4 +cAMP

— S6Bc

RL65

— BOVINE PITUITARY

FIG. 4

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:1:

Val Leu Thr Glu Glu Thr Glu Ile Ile Met Pro Thr Pro Lys Pro
1               5                       10                      15

Glu Leu Xaa Ala Xaa Xaa Asn
            20          22

( 2 ) INFORMATION FOR SEQ ID NO:2:

( i ) SEQUENCE CHARACTERISTICS:
( A ) LENGTH: 23 amino acids
( B ) TYPE: amino acid
( D ) TOPOLOGY: linear ( x i ) SEQUENCE DESCRIPTION: SEQ ID NO:2:

Ala Val Asn Pro Thr Gly Arg Asp Ala Val Glu Pro Val Ala Val
1               5                       10                      15

Xaa Ala Leu Asp Leu Ile Asn Lys
            20              23

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( x i ) SEQUENCE DESCRIPTION: SEQ ID NO:3:

Met Tyr Ala Pro Glu Tyr
1           5   6

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( D ) TOPOLOGY: linear ( x i ) SEQUENCE DESCRIPTION: SEQ ID NO:4:

Met Ile Phe Ala Leu Leu Phe Phe Gly
1           5                   9

( 2 ) INFORMATION FOR SEQ ID NO:5:

( i ) SEQUENCE CHARACTERISTICS:
        ( A ) LENGTH: 57 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

TAATTCAGGT TTAGGAGTAG GAGTAGGCAT AATAATTTCA GTTTCTTCAG 50

TTAAAAC 57

RECEPTOR POLYPEPTIDES AND THEIR PRODUCTION AND USES

BACKGROUND OF THE INVENTION

1. Field of the Invention

This invention relates to the cloning and expression of the cellular receptor molecules that are capable of binding the TGF-$\beta$ supergene family of proteins. The invention further relates to methods of production of the isolated receptor molecules and their uses.

2. Description of Related Art

Following the initial purification and characterization of transforming growth factor-beta (TGF-$\beta$) as a homodimeric, 25-Kd peptide (Frolik et al., *Proc. Natl. Acad. Sci. U.S.A.*, 80: 3676-3680 [1983]; Assoian et al., *J. Biol. Chem.*, 258: 7155-7160 [1983]; Roberts et al., *Biochemistry*, 22: 5692-5698 [1983]), there has been an exponential increase in knowledge relating to this molecule. The cloning of TGF-$\beta$1 and the resultant elucidation of its precursor structure (Derynck et al., *Nature*, 316: 701-705 [1985]) have led to the identification of at least four other forms of TGF-$\beta$ and the definition of a larger gene family comprising many other structurally related, but functionally distinct, regulatory proteins.

There are now many polypeptides that belong to the TGF-$\beta$ supergene family by virtue of amino acid homologies, particularly with respect to the conservation of seven of the nine cysteine residues of TGF-$\beta$ among all known family members. These include the mammalian inhibins (Mason et al., *Nature*, 318: 659-663 [1985]) and activins (Ling et al., *Nature*, 779-782 [1986]), and Mullerian inhibitory substance (MIS; Cate et al., *Cell*, 45: 685-698 [1986]), as well as the predicted products of both a pattern gene in Drosophila (the decapentaplegic gene complex, DPP-C; Padgett et al., *Nature*, 325: 81-84 [1987]), and an amphibian gene expressed in frog oocytes (Vg1; Weeks and Melton, *Cell*, 51: 861-867 [1987]). Most recently, three new proteins, called bone morphogenetic proteins (BMPs), have been added to the family. One subset of these proteins, BMP-2A and 2B, shares about 75% sequence identity with DPP-C and may represent the mammalian equivalent of that protein. Wozney et al., *Science*, 242: 1528-1534 (1988); Wang et al., *Proc. Natl. Acad. Sci. U.S.A.*, 85: 9484-9488 (1988).

In every case where the information is available, all polypeptides belonging to this family are encoded as larger precursors. The family resemblance is limited to the C-terminus of the precursor corresponding to the processed mature TGF-$\beta$ (Padgett et al., supra). With the exception of MIS, the C-terminal region is cleaved from the precursor at a pair of arginine residues. Although the position of this cleavage site varies among the family members, the C-terminus of all of the peptides is in the identical position, ending in the sequence where a cysteine residue is linked to the N-terminus of X-Cys-X (X being any amino acid), but differing in every case from the TGF-$\beta$ consensus C-terminal sequence where Cys is connected to the N-terminus of Lys-Cys-Ser.

A unifying feature of the biology of these polypeptides is their ability to regulate developmental processes. MIS induces regression of the female rudiments of the developing male reproductive system. The inhibins and activins, as discussed further below, regulate reproductive functions and erythropoietic activity. The BMPs are thought to play a role in the formation of cartilage and bone in vivo. DPP-C directs dorsal-ventral patterning in the developing fly embryo. Vg1 is postulated to be involved in the process of induction of mesoderm from ectoderm during gastrulation in the amphibian embryo. In amphibians, TGF-$\beta$ itself (Kimelman and Kirschner, *Cell*, 51: 869-877 [1987]) has been shown to augment the ability of fibroblast growth factor to induce mesoderm and plays a pivotal role in morphogenesis and organogenesis in mammalian embryos. In addition, like activin, TGF-$\beta$ is reported to possess follicle-stimulating-hormone (FSH)-releasing activity. Ying et al., *Biochem. Biophys. Res. Commun.*, 135: 950-956 (1986).

Inhibin is a glycoprotein produced by diverse tissues, including the gonads, pituitary, brain, bone marrow, placenta, and adrenal gland. It was initially identified by its ability to inhibit the secretion of FSH by the pituitary. DeJong and Sharpe, *Nature*, 263: 71-72 (1976); Schwartz and Channing, *Proc. Natl. Acad. Sci. U.S.A.*, 74: 5721-5724 (1977). Such preferential regulation of the gonadotropin secretion has generated a great deal of interest and prompted many laboratories in the past fifty years to attempt to isolate and characterize this substance from extracts of testis, spermatozoa, rete testis fluid, seminal plasma, and ovarian follicular fluid using various bioassays. Rivier et al., *Biochem. Biophys. Res. Commun.*, 133: 120 (1985); Ling et al., *Proc. Natl. Acad. Sci. U.S.A.*, 82: 7217 (1985); Fukuda et al., *Mol. Cell Endocrinol.*, 44: 55 (1985). The structure of inhibin, characterized from several species, consists of two disulfide-linked subunits: an $\alpha$ and either a $\beta_A$ or $\beta_B$ chain, designated "inhibin A" and "inhibin B, " respectively.

After the identification of inhibin, activin was shown to exist in follicular fluid as a naturally occurring substance. Activin was found to be capable of stimulating FSH release by rat anterior pituitary cells. Vale et al., *Nature*, 321: 776-779 (1986); Ling et al., *Nature*, (1986), supra. Activin consists of a homodimer or heterodimer of inhibin $\beta$ subunits, which may be $\beta_A$ or $\beta_B$ subunits. Vale et al., *Recent Prog. Horm. Res.*, 44: 1-34 (1988). There is 95-100% amino acid conservation of $\beta$ subunits among human, porcine, bovine, and rate activins. The $\beta_A$ and $\beta_B$ subunits within a given species are about 64-70% homologous. The activin $\beta_A$ and $\beta_B$ homodimers ("activin A" and "activin B," respectively) have been identified in follicular fluid, and both molecules have been cloned and their genes expressed. Mason et al., *Biochem, Biophys. Res. Commun.*, 135: 957 (1986); U.S. Pat. No. 4,798,885 issued 17 January 1989; Mason et al., *Molecular Endocrinol.*, 3: 1352-1358 (1989). The complete sequence of the $\beta_B$ subunit is published in Serono Symposium Publications, *Inhibin-Non-Steroidal Regulation of Follicle Stimulating Hormone Secretion*, eds. H. G. Burger et al., abstract by A. J. Mason et al., vol. 42, pp. 77-88 (Raven Press: New York, 1987), entitled "Human Inhibin and Activin: Structure and Recombinant Expression in Mammalian Cells."

Both activin A and activin AB (the $\beta_A\beta_B$ heterodimer), but thus far not activin B, have been isolated from natural sources. Activin mRNA ($\beta_A$ and $\beta_B$ subunits), bioactivity, and immunoactivity have been reported to be produced by testicular Leydig cells from immature rat and pig. Lee et al., *Science*, 243: 396-398 (1989); Lee et al., in Serono Symposium Publications, *The Molecular and Cellular Endocrinology of the Testis*, eds. Cooke and Sharpe, vol. 50, pp. 21-27 (Raven Press: New York, 1988). Activin A has been found recently to have erythropoietic-stimulating activity as well as FSH-releasing activity. EP Publ. No. 210,461 published Feb. 4, 1987 (where the protein is called BUF-3); Eto et al., *Biochem. Biophys. Res. Commun.*, 142: 1095-1103 (1987); Murata et al., *Proc. Natl. Acad. Sci. U.S.A.*, 85: 2434-2438 (1988) (where the activin is called EDF); Yu et al., *Nature*, 330: 765-767 (1987) (where the activin is called FRP). In these systems, inhibin antagonized the actions of activin.

Recently, the expression of inhibin subunits, each encoded by a separate gene, was demonstrated in several tissues in addition to ovary and testis. Inhibin $\alpha$, $\beta_A$, and $\beta_B$ mRNAs were detected in placental, pituitary, adrenal, bone marrow, and brain tissues. Meunier et al., *Proc. Natl. Acad. Sci. U.S.A.*, 85: 247-251 (1988). The expression of the inhibin subunit mRNAs varied by several-fold in a tissue-specific manner, suggesting different functions for these proteins depending on their pattern of association and their site of production.

In the human, growing preovulatory follicles and corpus luteum secrete inhibin into the circulation in response to FSH stimulation. Lee and Gibson, *Aust. J. Biol. Sci.*, 38: 115-120 (1985); McLachlan et al., *Fertil. Steril.*, 48: 1001 (1987). Thus, inhibin-related peptides play important roles in the modulation of gonadal functions via a pituitary feedback loop. In rat primary cultures of testis cells and ovarian thecal-interstitial cells, inhibin has been reported to enhance androgen biosynthesis stimulated by leutinizing hormone (LH), whereas activin suppresses androgen production. Hsueh et al., *Proc. Natl. Acad. Sci. U.S.A.*, 84: 5082-5086 (1987). Other workers have been unable to repeat these observations. deKretser and Robertson, *Biology of Reproduction*, 40: 33-47 (1989). Human ovarian theca were also shown to have a decrease in androgen production. It has now been shown that inhibin increases female fertility and activin decreases follicular size when they are administered locally to the ovaries. Woodruff et al., *Endocrinol.*, 127: 3196-3205 (1990). On the other hand, activin was found to stimulate spermatogonial proliferation in germ-sertoli cell co-cultures from immature rat testis. Mather et al., *Endocrinology*, 127: 3206-3214 (1990).

It appears that each of the polypeptides in the TGF-$\beta$ supergene family has at least one unique receptor. Thus, although TGF-$\beta$1 and TGF-$\beta$2 compete for receptor binding (Cheifetz et al., *Cell*, 48: 409-415 [1987]; Segarini et al., *J. Biol. Chem.*, 262: 14655-14662 [1987]), neither inhibin nor activin can compete for binding of TGF-$\beta$1 to a variety of cell types, including pituitary cells (Cheifetz et al., *J. Biol. Chem.*, 263: 16984-16991 [1988]), in which both TGF-$\beta$ and the activins elicit secretion of FSH, while inhibin antagonizes that activity. Ying et al., supra; Ying et al., *Biochim. Biophys. Res. Commun.*, 136: 969-975 [1986].

TGF-$\beta$ has been found to bind to nearly 150 different cell types and cell lines, and with only a few exceptions the cells bind TGF-$\beta$ with affinities in the picomolar range. Frolik et al., *J. Biol. Chem.*, 259: 10995-11000 (1984); Tucker et al., *Proc. Natl. Acad. Sci. U.S.A.*, 81: 6757-6761 (1984); Massague and Like, *J. Biol. Chem.*, 260: 2636-2645 (1985); Wakefield et al., *J. Cell. Biol.*, 105: 965-975 (1987).

Crosslinking of labeled TGF-$\beta$ to membrane receptors with disuccinimidyl suberate has revealed three distinct classes of integral cell membrane components that bind TGF-$\beta$ specifically and with high affinity. Massague, *J. Biol. Chem.*, 260: 7059-7066 [1985]; Massague and Like, *J. Biol. Chem.*, 260: 2636-2645 (1985); Cheifetz et al., *J. Biol. Chem.*, 261: 9972-9978 (1986); Segarini and Seyedin, *J. Biol. Chem.*, 263: 8366-8370 (1988); Cheifetz et al., *J. Biol. Chem.*, supra; Cheifetz et al., *J. Biol. Chem.*, 263: 10783-10789 (1988). Class I components are 65 Kd in all species, whereas class II components range from 85 Kd in rodent cells to 95 Kd in monkey and human cells to 110 Kd in chicken cells. The binding of the various forms of TGF-$\beta$ to both class I and II receptors is in the order TGF-$\beta$1>TGF-$\beta$1.2>TGF-$\beta$2. Cheifetz et al., *J. Biol. Chem.*, supra. In contrast, all three forms of TGF-$\beta$ bind equivalently to class III receptors, which represent the most abundant cross-linked species. This form is generally considered to be dimeric (Massague, *J. Biol. Chem.*, 260: 7059-7066, supra) and to be composed of proteoglycan subunits of 250-350 Kd (Segarini and Seyedin, supra; Cheifetz et al., *J. Biol. Chem.*, 16984-16991, supra). Another subset of this high-molecular-weight component has also been described that preferentially binds TGF-$\beta$2. Segarini et al., *J. Biol. Chem.*, 262: 14655-14662 (1987). Most frequently, all three classes of these binding proteins coexist on cells.

Class I and II TGF-$\beta$ receptor components, like most growth factor receptors, are glycoproteins. Most of the carbohydrate is N-linked and contributes approximately 5 Kd and 15-20 Kd to the mass of components I and II, respectively. Cheifetz et al., *J. Biol. Chem.*, 16984-16991, supra. In contrast to all other known polypeptide receptors, the class III protein is a proteoglycan consisting predominantly of heparin sulfate glycosaminoglycan chains with a smaller amount of chondroitin or dermatan sulfate attached to a core protein of about 100-140 Kd. The binding site for TGF-$\beta$ resides in this core protein. Segarini and Seyedin, supra; Cheifetz et al., *J. Biol. Chem.*, 16904-16991, supra.

There is considerable controversy concerning the roles of the various classes of proteins that cross-link to TGF-$\beta$. Cheifetz and coworkers have proposed that class III receptors mediate all functions of TGF-$\beta$ in which TGF-$\beta$1 and TGF-$\neq$2 have been shown to be equipotent; this includes regulation of extracellular matrix as well as most effects on growth and differentiation. Cheifetz et al., 1987 and 1988, supra. Moreover, they suggest that biological activities specific to TGF-$\beta$1 are mediated through the class I and II receptors; these would include the reported selective inhibitory activity of TGF-$\beta$1 on growth of either B6SUt-A multipotential hematopoietic progenitor cells (Cheifetz et al., *J. Biol. Chem.*, 10783-10789, supra) or endothelial cells. Jennings et al., *J. Cell Physiol.*, 137: 167-172 (1988). In contrast, it has been shown that class III binding is not exhibited by primary epithelial, endothelial, and lymphoid cells and may not be necessary for many biological activities of TGF-$\beta$. Segarini et al., *Mol. Endocrin.*, 3: 261-272 (1989). Thus, cells such as L-6 myoblasts (Segarini et al., 1987, supra) and primary lymphocytes (Kehrl et al., *J. Immunol.*, 143, 1868-1874 [1989]), which respond equally well to TGF-$\beta$1 and TGF-$\beta$2, have only class I and II receptors. In addition, preliminary data demonstrate that selection of cell mutants resistant to the action of TGF-$\beta$ results in the isolation of lines that have selectively lost the type I TGF-$\beta$ binding.

Although their occurrence is rather rare, several neoplastic cells appear to lack these putative TGF-$\beta$ receptors. These include the PC12 rat pheochromocytoma, human retinoblastoma cells, and several leukemic cell lines. Kimchi et al., *Science*, 240: 196-198 (1988); Keller et al., *J. Cell. Biochem.*, 39: 175-184 (1989). In each of these cases, the lack of receptor proteins correlates with resistance of the cells to the inhibitory effects of TGF-β, and it has been proposed that loss of TGF-β receptors might be a mechanism whereby pre-neoplastic cells could progress to tumor cells by escaping from negative growth. Sporn and Roberts, *Nature*, 313: 745-747 (1985).

Yet another anomaly of TGF-β binding in tumor cells has been reported. Although the binding of TGF-β to cells has been shown to be specific, a novel 70-74 Kd complex has been reported on $GH_3$ rat pituitary tumor cells that binds not only TGF-β1, but also TGF-β2, activin AB, and inhibin with lower affinity. Cheifetz et al., *J. Biol. Chem.*, 263: 17225-17228 (1988). The biological function of this complex is not known.

Although it has long been known or suspected that the biological effects of inhibin and activin are mediated via interaction with a cellular receptor molecule present on the surface of target cells, to date such receptor(s) have never been isolated or identified. While a protein designated as an "activin receptor" has been expression cloned (Mathews and Vale, *Cell*, 65: 1-20 [1991]), it does not appear to be a mammalian receptor in that it is a serine kinase (not found in mammalian cells), and it is most closely related to the *C. elegans* daf-1 gene product (found in nematodes).

It is an object of the present invention to isolate and specifically identify and purify the cellular receptors to which the TGF-β supergene family is capable of binding in vivo.

A more specific object of the present invention is to identify and isolate the cellular receptors to which inhibin and/or activin binds in vivo.

It is another object to provide nucleic acid molecules encoding such receptors.

It is yet another object to provide derivatives and modified forms of the TGF-β supergene family of receptors, including amino acid sequence variants and covalent derivatives thereof.

These and other objects of the invention will be apparent to the ordinary artisan upon consideration of the specification as a whole.

SUMMARY OF THE INVENTION

Accordingly, this invention provides an isolated TGF-β supergene family (TSF) receptor polypeptide, which may be antigenically or biologically active. Preferably this receptor polypeptide is the inhibin/activin receptor polypeptide.

In another aspect, this invention provides an isolated antibody capable of binding to the polypeptide. In a still further embodiment, the invention provides a method for detecting the TSF receptor polypeptide in vitro or in vivo comprising contacting the antibody with a sample or cell suspected of containing the receptor polypeptide and detecting if binding has occurred.

In still another aspect, a method is provided for purifying molecules that bind to a TSF receptor polypeptide comprising contacting a sample containing the molecules to be purified with the receptor polypeptide immobilized on a support under conditions whereby the molecules to be purified are selectively adsorbed onto the immobilized receptor, washing the immobilized support to remove non-adsorbed material, and separating the molecules to be purified from the immobilized receptor polypeptide to which they are adsorbed.

In yet another aspect, this invention provides a method of determining the presence in a test sample of a molecule that binds to TSF receptor polypeptide (and preferably also has TSF biological activity) comprising contacting the test sample with the receptor polypeptide and determining if binding has occurred. In still further embodiments, the invention provides an isolated TSF receptor nucleic acid molecule.

In a still further aspect, the invention provides a pharmaceutical composition comprising the TSF receptor polypeptide in a pharmaceutically acceptable carrier and a method for blocking an excess amount of a TSF member in a mammal comprising administering to the mammal an effective amount of the receptor polypeptide.

BRIEF DESCRIPTION OF THE DRAWINGS

FIG. 2A shows analysis of inhibin-FITC using size-exclusion chromatography, with the insert showing hormone conjugate following reduction, and FIG. 2B shows analysis of activin-FITC using size-exclusion chromatography, with the insert showing hormone conjugate following reduction.

FIG. 4 shows slot blots of inhibin/activin receptor RNA in various mouse and bovine cell lines.

DESCRIPTION OF THE PREFERRED EMBODIMENTS

1. Terms Employed

Figure 1:
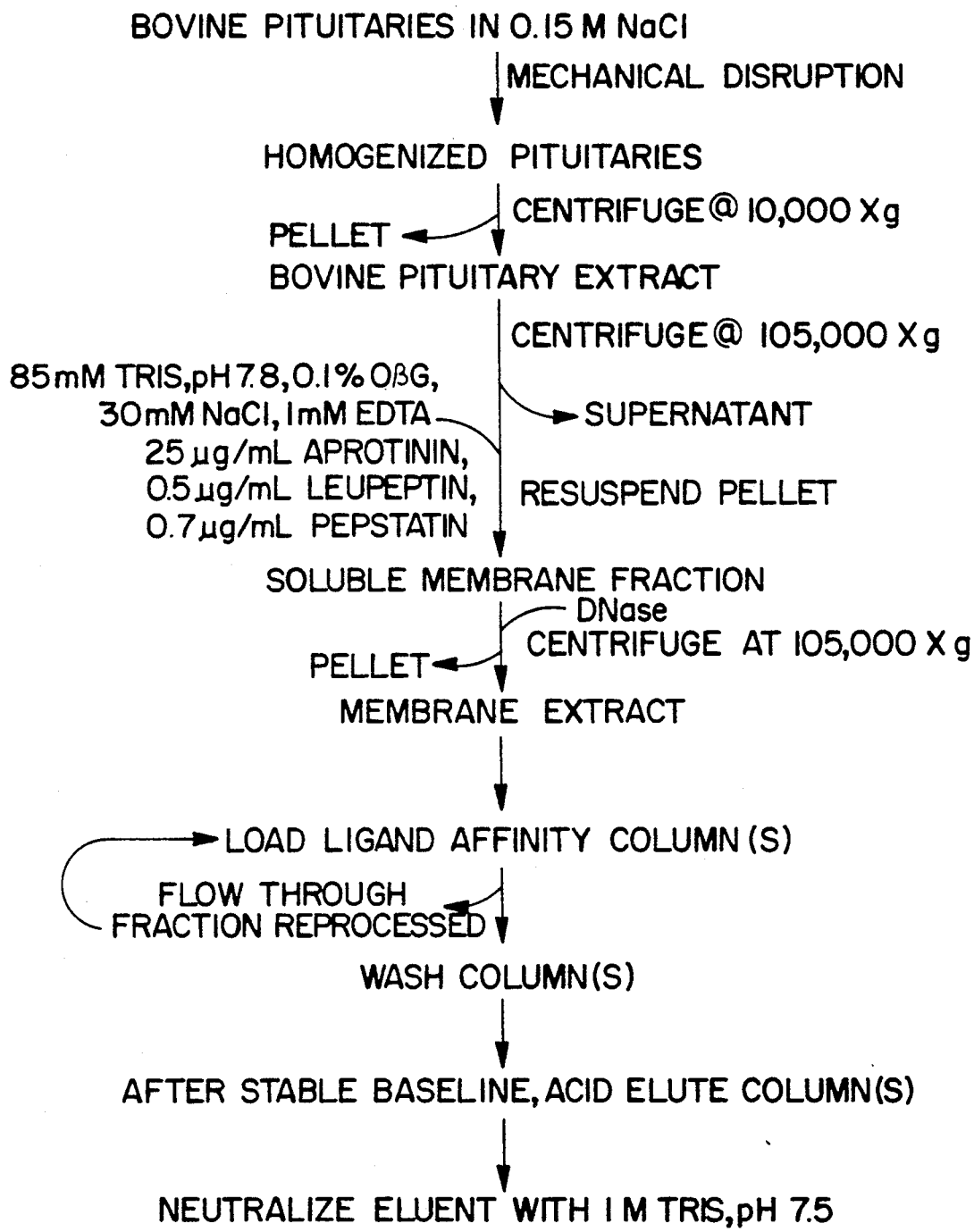
FIG. 1 depicts the schematic diagram for isolation of inhibin/activin receptor from bovine pituitaries.

In accordance with the present invention, a "TGF-β supergene family (or TSF) receptor polypeptide" is defined herein to be any polypeptide that possesses a biological property of a mature receptor to which at least one member of the TGF-β supergene family binds. Members of this family include inhibins, activins, MIS, DPP-C, Vg1, and BMPs.

In accordance with the present invention, an "inhibin/activin receptor polypeptide" is defined herein to be any polypeptide that possesses a biological property of the mature human inhibin/activin receptor described herein.

"Biological property" for the purposes herein means an in vivo effector or antigenic function or activity that is directly or indirectly performed by the mature receptor (whether in its native or denatured conformation). Effector functions include ligand binding, any carrier binding activity, or any structural role. However, effector functions do not include possession of an epitope or antigenic site that is capable of cross-reacting with antibodies raised against the particular mature receptor polypeptide. An antigenic function means possession of an epitope or antigenic site that is capable of cross-reacting with antibodies raised against the mature receptor.

Biologically active TSF receptor polypeptide is defined herein as a polypeptide that shares an effector function of the mature receptor and that also may (but need not) possess an antigenic function. A principal known effect or function of the receptor polypeptide herein is binding to at least one TSF member. For example, the inhibin/activin receptor polypeptide binds to inhibin A, inhibin B, activin A, activin AB, and/or activin B, depending on whether the receptor polypeptide is one for activin or inhibin.

Antigenically active TSF receptor polypeptide is defined as a polypeptide that possesses an antigenic function of the mature TSF receptor and that also may (but need not) possess an effector function.

In preferred embodiments, antigenically active TSF receptor polypeptide is a polypeptide that binds with an affinity of at least about $10^6$ l/mole to an antibody raised against the mature human TSF receptor. Ordinarily, the polypeptide binds with an affinity of at least about $10^7$ l/mole. Most preferably, the antigenically active TSF receptor polypeptide is a polypeptide that binds to an antibody raised against the mature human TSF receptor sequence in its native conformation. The mature human TSF receptor sequence in its native conformation is the human receptor as found in nature that has not been denatured by chaotropic agents, heat, or other treatment that substantially modifies the three-dimensional structure of the human TSF receptor as determined, for example, by migration on non-reducing, non-denaturing sizing gels. Antibody used in this determination is rabbit polyclonal antibody raised by formulating native human TSF receptor in Freund's complete adjuvant, subcutaneously injecting the formulation, and boosting the immune response by intraperitoneal injection of the formulation until the titer of anti-TSF receptor antibody plateaus.

Ordinarily, biologically or antigenically active TSF receptor polypeptide will have an amino acid sequence having at least 70% amino acid sequence identity with the native mature human inhibin/activin receptor sequence, more preferably at least 75%, more preferably at least 80%, more preferably at least 85%, more preferably at least 90%, and most preferably at least 95%. Identity or homology with respect to the native mature human inhibin/activin sequence is defined herein as the percentage of amino acid residues in the candidate sequence that are identical with the residues in the mature human inhibin/activin receptor sequence after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the mature human inhibin/activin receptor sequence shall be construed as affecting sequence identity or homology.

Thus, the biologically active and antigenically active TSF receptor polypeptides that are the subject of this invention include prepro-inhibin/activin receptor; pro-inhibin/activin receptor; mature inhibin/activin receptor; fragments thereof having a consecutive sequence of at least 5, 10, 15, 20, 25, 30, or 40 amino acid residues from any of the above sequences; amino acid sequence variants of any of the above sequences wherein an amino acid residue has been inserted N- or C-terminal to, or within, the prepro-, pro-, pre-, or mature human inhibin/activin receptor amino acid sequence or its fragment as defined above; amino acid sequence variants of the prepro-, pro-, pre-, or mature human inhibin/activin receptor amino acid sequence or its fragment as defined above wherein an amino acid residue of any of these sequences or fragment thereof has been substituted by another residue, including predetermined mutations by, e.g., site-directed or PCR mutagenesis, and other mammalian species of the inhibin/activin receptor such as human, rabbit, rat, porcine, non-human primate, equine, murine, and ovine inhibin/activin receptor and alleles or other naturally occurring variants of the foregoing and human sequences; derivatives of the inhibin/activin receptor or its fragments as defined above wherein the inhibin/activin receptor or its fragments have been covalent modified, by substitution, chemical, enzymatic, or other appropriate means, with a moiety other than a naturally occurring amino acid; glycosylation variants of inhibin/activin receptor polypeptide (insertion of a glycosylation site or deletion of any glycosylation site by deletion, insertion, or substitution of suitable residues); and soluble forms of the inhibin/activin receptor such as those that lack a functional transmembrane domain. Such fragments and variants exclude any polypeptide heretofore identified, including any known TSF receptors of any animal species or any known polypeptide fragment that are anticipatory under 35 USC §102 as well as polypeptides obvious thereover under 35 USC §103. The preferred TSF receptor polypeptide is the inhibin/activin receptor polypeptide, more preferably, the bovine or human mature inhibin/activin receptor.

"Isolated" TSF receptor polypeptide means a TSF receptor polypeptide that has been purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain.

In accordance with this invention, a TSF receptor nucleic acid molecule is RNA or DNA containing greater than ten bases that encodes a biologically active or antigenically active TSF receptor polypeptide, is complementary to nucleic acid sequence encoding such TSF receptor polypeptide, or hybridizes to nucleic acid sequence encoding such TSF receptor polypeptide and remains stably bound to it under stringent conditions.

Preferably, the TSF receptor nucleic acid molecule encodes a polypeptide sharing at least 70% sequence identity, more preferably at least 80%, still more preferably at least 85%, even more preferably at least 90%, and most preferably 95%, with the sequence of mature human inhibin/activin receptor polypeptide. Preferably, the TSF receptor nucleic acid molecule that hybridizes to the mature human inhibin/activin receptor nucleic acid sequence contains at least 20, more preferably 40, and most preferably 90 bases. Such hybridizing or complementary nucleic acid molecule, however, is further defined as being novel under 35 USC §102 and unobvious under 35 USC §103 over any prior art nucleic acid molecules, including those that encode, hybridize under stringent conditions, or are complementary to nucleic acid molecules encoding a known TSF receptor polypeptide.

Stringent conditions are those that (1) employ low ionic strength and high temperature for washing, for example, 0.015M NaCl/0.0015M sodium citrate/0.1% NaDodSO$_4$ at 50 C; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

An isolated TSF receptor nucleic acid molecule is a nucleic acid molecule that is identified and separated from at least one contaminant nucleic acid molecule with which it is ordinarily associated in the natural source of the TSF receptor nucleic acid. An isolated TSF receptor nucleic acid molecule is other than in the form or setting in which it is found in nature. Isolated TSF receptor nucleic acid molecules therefore are distinguished from the TSF receptor nucleic acid molecule as it exists in natural cells. However, an isolated TSF receptor nucleic acid molecule includes TSF receptor nucleic acid molecules contained in cells that ordinarily express TSF receptor polypeptide where, for example, the nucleic acid molecule is in a chromosomal location different from that of natural cells.

The isolated TSF receptor polypeptide or TSF receptor nucleic acid may be labeled for diagnostic and probe purposes, using a label as described and defined further below in the discussion of diagnostic assays.

Isolated antibody capable of binding to TSF receptor polypeptide is an antibody that binds to the polypeptide with an affinity of at least about $10^6$ l/mole, preferably at least about $10^7$ l/mole, and is identified and separated and/or recovered from a component of any natural environment in which it may be present.

Molecules that bind to TSF receptor polypeptide and have TSF biological activity are those organic molecules and polypeptides that will bind to TSF receptor polypeptide under both in vitro and in vivo conditions. TSF biological activity means at least one inherent biological property (excluding any immunological properties) of a TSF member in its native conformation. For example, inhibin biological activity includes such properties as FSH-inhibitory activity, increase in female fertility when administered locally to the ovary, effects on K562 cell hemoglobin production (inhibition of activin-stimulated production), and fetal hemoglobin switching activity.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

An "exogenous" element is defined herein to mean nucleic acid sequence that is foreign to the cell, or homologous to the cell but in a position within the host cell nucleic acid in which the element is ordinarily not found.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Restriction enzyme digestion" of DNA refers to catalytic cleavage of the DNA with an enzyme that acts only at certain locations in the DNA. Such enzymes are called restriction endonucleases, and the site for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1–2 units of enzyme in about 20 μl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., *Molecular Cloning: A Laboratory Manual* [New York: Cold Spring Harbor Laboratory Press, 1989].

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9: 6103-6114 (1981), and Goeddel et al., *Nucleic Acids Res.* 8: 4057 (1980).

"Southern analysis" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37-9.52 of Sambrook et al., supra.

"Northern analysis" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra.

"Ligation" refers to the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25-1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froehler et al., *Nucl. Acids Res.*, 14: 5399-5407 [1986]. Further methods include the polymerase chain reaction defined below and other autoprimer methods and oligonucleotide syntheses on solid supports. All of these methods are described in Engels et al., *Agnew. Chem. Int. Ed. Engl.*, 28: 716-734 [1989]). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotide are then purified on polyacrylamide gels.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued 28 July 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51: 263 (1987); Erlich, ed., *PCR Technology*, (Stockton Press, N.Y., 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

2. Preparation of Natural Sequence TSF Receptor Polypeptide

Most of the discussion below pertains to production of the TSF receptor polypeptide by culturing cells transfected to express TSF receptor nucleic acid (typically by transforming with an expression vector) and recovering the polypeptide from the cells. It is further envisioned that the TSF receptor polypeptide of this invention may be produced by homologous recombination, or with recombinant production methods utilizing control elements introduced into cells already containing DNA encoding the TSF receptor currently in use in the field. For example, a powerful promoter/enhancer element, a suppressor, or an exogenous transcription modulatory element is inserted in the genome of the intended host cell in proximity and orientation sufficient to influence the transcription of DNA encoding the desired receptor polypeptide. The control element does not encode the receptor polypeptide of this invention, but the DNA is present in the host cell genome. One next screens for cells making the receptor polypeptide of this invention, or for increased or decreased levels of expression, as desired.

Thus, the invention contemplates a method for producing TSF receptor polypeptide comprising inserting into the genome of a cell containing the TSF receptor nucleic acid molecule a transcription modulatory element in sufficient proximity and orientation to the nucleic acid molecule to influence transcription thereof, with an optional further step comprising culturing the cell containing the transcription modulatory element and the nucleic acid molecule. The invention also contemplates a host cell containing the TSF receptor nucleic acid molecule operably linked to exogenous control sequences recognized by the host cell. In addition, the invention relates to a method for obtaining cells having increased or decreased transcription of the TSF receptor nucleic acid molecule comprising:

1(a) providing cells containing the nucleic acid molecule;

(b) introducing into the cells a transcription modulating element; and (c) screening the cells for a cell in which the transcription of the nucleic acid molecule is increased or decreased.

A. Isolation of DNA Encoding TSF Receptor Polypeptide

The DNA encoding TSF receptor polypeptide may be obtained from any cDNA library prepared from tissue believed to possess the TSF receptor mRNA and to express it at a detectable level. The TSF receptor gene may also be obtained from a genomic library or by in vitro oligonucleotide synthesis as defined above assuming the complete nucleotide or amino acid sequence is known.

Libraries are screened with probes designed to identify the gene of interest or the protein encoded by it. For cDNA expression libraries, suitable probes include monoclonal or polyclonal antibodies that recognize and specifically bind to the TSF receptor; oligonucleotides of about 20–80 bases in length that encode known or suspected portions of the TSF receptor cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding TSF receptor is to use PCR methodology as described in section 14 of Sambrook et al., supra. This method requires the use of oligonucleotide probes that will hybridize to the TSF receptor polypeptide. Strategies for selection of oligonucleotides are described below.

A preferred method of practicing this invention is to use carefully selected oligonucleotide sequences to screen cDNA libraries from various tissues, preferably mammalian pituitary cell lines. More preferably, human pituitary cell line cDNA libraries are screened with the oligonucleotide probes.

The oligonucleotide sequences selected as probes should be of sufficient length and sufficiently unambiguous that false positives are minimized. The actual nucleotide sequence(s) is usually based on conserved or highly homologous nucleotide sequences or regions of the TSF receptor molecule. The oligonucleotides may be degenerate at one or more positions. The use of degenerate oligonucleotides may be of particular importance where a library is screened from a species in which preferential codon usage is not known.

The oligonucleotide must be labeled such that it can be detected upon hybridization to DNA in the library being screened. The preferred method of labeling is to use 32-P labeled ATP with polynucleotide kinase, as is well known in the art, to radiolabel the oligonucleotide. However, other methods may be used to label the oligonucleotide, including, but not limited to, biotinylation or enzyme labeling.

Of particular interest is the TSF receptor nucleic acid that encodes a full-length polypeptide. In some preferred embodiments, the nucleic acid sequence includes the native TSF receptor signal sequence. Nucleic acid having all the protein coding sequence is obtained by screening selected cDNA or genomic libraries using the deduced amino acid sequence disclosed herein for the first time, and, if necessary, using conventional primer extension procedures as described in section 7.79 of Sambrook et al., supra, to detect precursors and processing intermediates of mRNA that may not have been reverse-transcribed into cDNA.

B. Amino Acid Sequence Variants of Native TSF Receptor

Amino acid sequence variants of TSF receptor are prepared by introducing appropriate nucleotide changes into the TSF receptor DNA, or by in vitro synthesis of the desired TSF receptor polypeptide. Such variants include, for example, deletions from, or insertions or substitutions of, residues within the amino acid sequence shown for the human inhibin/activin receptor in FIG. 1. Any combination of deletion, insertion, and substitution is made to arrive at the final construct, provided that the final construct possesses the desired characteristics. The amino acid changes also may alter post-translational processes of the TSF receptor, such as changing the number or position of glycosylation sites, altering the membrane anchoring characteristics, and/or altering the intracellular location of the TSF receptor by inserting, deleting, or otherwise affecting the leader sequence of the TSF receptor.

For the design of amino acid sequence variants of the TSF receptor, the location of the mutation site and the nature of the mutation will depend on the TSF receptor characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the TSF receptor polypeptide that are preferred locations for mutagenesis is called "alanine scanning mutagenesis," as described by Cunningham and Wells, Science, 244: 1081–1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed TSF receptor variants are screened for the optimal combination of desired activity.

There are two principal variables in the construction of amino acid sequence variants: the location of the mutation site and the nature of the mutation. For example, variants of the inhibin/activin receptor polypeptide include variants from the FIG. 1 sequence, and may represent naturally occurring alleles (which will not require manipulation of the inhibin/activin receptor DNA) or predetermined mutant forms made by mutating the DNA, either to arrive at an allele or a variant not found in nature. In general, the location and nature of the mutation chosen will depend upon the TSF receptor characteristic to be modified. Obviously, such variations that, for example, convert TSF receptor into a known polypeptide such as inhibin, activin, a BMP, or TGF-β are not included within the scope of this invention, nor are any other TSF receptor variants or polypeptide sequences that are not novel and unobvious over the prior art.

Amino acid sequence deletions generally range from about 1 to 30 residues, more preferably about 1 to 10 residues, and typically are contiguous. Contiguous deletions ordinarily are made in even numbers of residues, but single or odd numbers of deletions are within the scope hereof. Deletions may be introduced into regions of low homology among the TSF receptors that share the most sequence identity to modify the activity of the TSF receptor. Or deletions may be introduced into regions of low homology among human inhibin/activin receptor and other mamalian inhibin/activin receptor polypeptides that share the most sequence identity to the human inhibin/activin receptor. Deletions from a mammalian TSF receptor polypeptide in areas of substantial homology with other mammalian TSF receptors will be more likely to modify the biological activity of the TSF receptor more significantly. The number of consecutive deletions will be selected so as to preserve the tertiary structure of TSF receptors in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature TSF receptor sequence) may range generally from about 1 to 10 residues, more preferably 1 to 5, most preferably 1 to 3. Insertions are preferably made in even numbers of residues, but this is not required. Examples of terminal insertions include mature TSF receptor with an N-terminal methionyl residue, an artifact of the direct expression of mature TSF receptor in recombinant cell culture, and fusion of a heterologous N-terminal signal sequence to the N-terminus of the mature TSF receptor molecule to facilitate the secretion of mature TSF receptor from recombinant hosts. Such signal sequences generally will be obtained from, and thus homologous to, the intended host cell species. Suitable sequences include STII or lpp for *E. coli*, alpha factor for yeast, and viral signals such as herpes gD for mammalian cells.

Other insertional variants of the TSF receptor molecule include the fusion to the N- or C-terminus of TSF receptor of immunogenic polypeptides (i.e., not endogenous to the host to which the fusion is administered), e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published 6 April 1989.

A third group of variants are amino acid substitution variants. These variants have at least one amino acid residue in the TSF receptor molecule removed and a different residue inserted in its place. The sites of greatest interest for substitutional mutagenesis include sites identified as the active site(s) of TSF receptor and sites where the amino acids found in the known analogues are substantially different in terms of side-chain bulk, charge, or hydrophobicity, but where there is also a high degree of sequence identity at the selected site among various TSF receptor species and/or within the various animal analogues of one TSF member.

Other sites of interest are those in which particular residues of the TSF receptor obtained from various family members and/or animal species within one member are identical. These sites, especially those falling within a sequence of at least three other identically conserved sites, are substituted in a relatively conservative manner. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the TSF receptor are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and (6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive to proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 1) or deleted. Alternatively, about 1-3 residues are inserted adjacent to such sites.

Any cysteine residues not involved in maintaining the proper conformation of the TSF receptor also may be substituted, generally with serine, to improve the oxidative stability of the molecule and prevent aberrant crosslinking.

Nucleic acid molecules encoding amino acid sequence variants of TSF receptor are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of TSF receptor polypeptide.

Oligonucleotide-mediated mutagenesis is a preferred method for preparing substitution, deletion, and insertion variants of TSF receptor DNA. This technique is well known in the art as described by Adelman et al., *DNA,* 2: 183 (1983). Briefly, TSF receptor DNA is altered by hybridizing an oligonucleotide encoding the desired mutation to a DNA template, where the template is the single-stranded form of a plasmid or bacteriophage containing the unaltered or native DNA sequence of TSF receptor. After hybridization, a DNA polymerase is used to synthesize an entire second complementary strand of the template that will thus incorporate the oligonucleotide primer, and will code for the selected alteration in the TSF receptor DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.,* 75: 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al. *Meth. Enzymol.,* 153: 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the TSF receptor, and the other strand (the original template) encodes the native, unaltered sequence of the TSF receptor. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding TSF receptor mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis is also suitable for making amino acid variants of TSF receptor polypeptide. While the following discussion refers to DNA, it is understood that the technique also finds application with RNA. The PCR technique generally refers to the following procedure (see Erlich, supra, the chapter by R. Higuchi, p. 61-70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 $\mu$g) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 $\mu$l. The reaction mixture is overlayed with 35 $\mu$l mineral oil. The reaction mixture is denatured for five minutes at 100° C., placed briefly on ice, and then 1 $\mu$l *Thermus aquaticus* (Taq) DNA polymerase (5 units/$\mu$l, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.
30 sec. 72° C., then 19 cycles of the following:
30 sec. 94° C.
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells et al., *Gene*, 34: 315 (1985). The starting material is the plasmid (or other vector) comprising the TSF receptor DNA to be mutated. The codon(s) in the TSF receptor DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the TSF receptor DNA. After the restriction sites have been introduced into the plasmid, the plasmid is cut at these sites linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TSF receptor DNA sequence.

C. Insertion of Nucleic Acid into a Replicable Vector

The nucleic acid (e.g., cDNA or genomic DNA) encoding native or variant TSF receptor polypeptide is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The TSF receptor of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the TSF receptor DNA that is inserted into the vector. The heterologous signal sequence selected should be one that is recognized and processed (i.e., cleaved by a signal peptidase) by the host cell. For prokaryotic host cells that do not recognize and process the native TSF receptor signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase, alpha factor, or acid phosphatase leaders, the *C. albicans* glucoamylase leader (EP 362,179 published 4 April 1990), or the signal described in WO 90/13646 published 15 November 1990. In mammalian cell expression the native signal sequence (i.e., the TSF receptor presequence that normally directs secretion of TSF receptor from its native mammalian cells in vivo) is satisfactory, although other mammalian signal sequences may be suitable, such as signal sequences from other TSF receptor polypeptides or from the same TSF receptor from a different animal species, signal sequences from a TSF member, including inhibin or activin, and signal sequences from secreted polypeptides of the same or related species, as well as viral secretory leaders, for example, the herpes simplex gD signal.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of TSF receptor DNA. However, the recovery of genomic DNA encoding TSF receptor is more complex than that of an exogenously replicated vector because restriction enzyme digestion is required to excise the TSF receptor DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 [1982]), mycophenolic acid (Mulligan et al., *Science*, 209: 1422 [1980], or hygromycin (Sugden et al., *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the TSF receptor nucleic acid, such as dihydrofolate reductase (DHFR) or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes TSF receptor polypeptide. Amplification is the process by which genes in greater demand for the production of a protein critical for growth are reiterated in tandem within the chromosomes of successive generations of recombinant cells. Increased quantities of TSF receptor are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. U.S.A.*, 77: 4216 [1980]. The transformed cells are then exposed to increased levels of Mtx. This leads to the synthesis of multiple copies of the DHFR gene, and, concomitantly, multiple copies of other DNA comprising the expression vectors, such as the DNA encoding TSF receptor. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells [particularly wild-type hosts that contain endogenous DHFR] transformed or co-transformed with DNA sequences encoding TSF receptor, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282: 39 [1979]; Kingsman et al., *Gene*, 7: 141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the TSF receptor nucleic acid. Promoters are untranslated sequences located upstream (5') to the start codon of a structural gene (generally within about 100 to 1000 bp) that control the transcription and translation of particular nucleic acid sequence, such as the TSF receptor nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to TSF-receptor-encoding DNA by removing the promoter from the source DNA by restriction enzyme digestion and inserting the isolated promoter sequence into the vector. Both the native TSF receptor promoter sequence and many heterologous promoters may be used to direct amplification and/or expression of the TSF receptor DNA. However, heterologous promoters are preferred, as they generally permit greater transcription and higher yields of expressed TSF receptor as compared to the native TSF receptor promoter.

Promoters suitable for use with prokaryotic hosts include the β-lactamase and lactose promoter systems (Chang et al., *Nature*, 275: 615 [1978]; and Goeddel et al., *Nature*, 281: 544 [1979]), alkaline phosphatase, a tryptophan (trp) promoter system (Goeddel, *Nucleic Acids Res.*, 8: 4057 [1980] and EP 36,776) and hybrid promoters such as the tac promoter (deBoer et al., *Proc. Natl. Acad. Sci. U.S.A.*, 80: 21–25 [1983]). However, other known bacterial promoters are suitable. Their nucleotide sequences have been published, thereby enabling a skilled worker operably to ligate them to DNA encoding TSF receptor (Siebenlist et al., *Cell*, 20: 269 [1980]) using linkers or adaptors to supply any required restriction sites. Promoters for use in bacterial systems also will contain a Shine-Dalgarno (S.D.) sequence operably linked to the DNA encoding TSF receptor polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; and Holland, *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

TSF receptor transcription from vectors in mammalian host cells is controlled, for example, by promoters obtained from the genomes of viruses such as polyoma virus, fowlpox virus (UK 2,211,504 published 5 July 1989), adenovirus (such as Adenovirus 2), bovine papilloma virus, avian sarcoma virus, cytomegalovirus, a retrovirus, hepatitis-B virus, and most preferably Simian Virus 40 (SV40), from heterologous mammalian promoters, e.g., the actin promoter or an immunoglobulin promoter, from heat-shock promoters, and from the promoter normally associated with the TSF receptor sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209: 1422–1427 (1980); Pavlakis et al., *Proc. Natl. Acad. Sci. U.S.A.*, 78: 7398–7402 (1981). The immediate early promoter of the human cytomegalovirus is conveniently obtained as a HindIII E restriction fragment. Greenaway et al., *Gene*, 18: 355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295: 503–508 (1982) on expressing cDNA encoding immune interferon in monkey cells; Reyes et al., *Nature*, 297: 598–601 (1982) on expression of human β-interferon cDNA in mouse cells under the control of a thymidine kinase promoter from herpes simplex virus; Canaani and Berg, *Proc. Natl. Acad. Sci. U.S.A.*, 79: 5166-5170 (1982) on expression of the human interferon β1 gene in cultured mouse and rabbit cells; and Gorman et al., *Proc. Natl. Acad. Sci. U.S.A.*, 79: 6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the TSF receptor of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. U.S.A.*, 78: 993 [1981]) and 3' (Lusky et al., *Mol. Cell Bio.*, 3: 1108 [1983]) to the transcription unit, within an intron (Banerji et al., *Cell*, 33: 729 [1983]), as well as within the coding sequence itself (Osborne et al., *Mol. Cell Bio.*, 4: 1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297: 17-18 (1982) on enhancing elements for activation of eukaryotic promoters. The enhancer may be spliced into the vector at a position 5' or 3' to the TSF-receptor-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding TSF receptor.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.*, 9: 309 (1981) or by the method of Maxam et al., *Methods in Enzymology*, 65: 499 (1980).

(viii) Transient Expression Vectors

Particularly useful in the practice of this invention are expression vectors that provide for the transient expression in mammalian cells of DNA encoding the TSF receptor polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17-16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of TSF receptor polypeptide that have TSF receptor polypeptide biological activity.

(ix) Suitable Exemplary Vertebrate Cell Vectors

Other methods, vectors, and host cells suitable for adaptation to the synthesis of TSF receptor in recombinant vertebrate cell culture are described in Gething et al., *Nature*, 293: 620-625 [1981]; Mantei et al., *Nature*, 281: 40-46 [1979]; Levinson et al.; EP 117,060; and EP 117,058. A particularly useful plasmid for mammalian cell culture expression of TSF receptor is pRK5 (EP pub. no. 307,247) or pSVI6B (U.S. Ser. No. 07/441,574 filed 22 November 1989, the disclosure of which is incorporated herein by reference).

D. Selection and Transformation of Host Cells

Suitable host cells for cloning or expressing the vectors herein are the prokaryote, yeast, or higher eukaryotic cells described above. Suitable prokaryotes include eubacteria, such as Gram-negative or Gram-positive organisms, for example, *E. coli*, Bacilli such as *B. subtilis*, Pseudomonas species such as *P. aeruginosa*, *Salmonella typhimurium*, or *Serratia marcescans*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryotes, eukaryotic microbes such as filamentous fungi or yeast are suitable hosts for TSF-receptor-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985], Kluyveromyces hosts (U.S. Pat. No. 4,943,529) such as, e.g., *K. lactis* [Louvencourt et al., *J. Bacteriol.*, 737 (1983)], *K. fragilis*, *K. bulgaricus*, *K. thermotolerans*, and *K. marxianus*, yarrowia [EP 402,226], *Pichia pastoris* [EP 183,070; Sreekrishna et al., *J. Basic Microbiol.*, 28: 265-278 (1988)], Candida, *Trichoderma reesia* [EP 244,234], *Neurospora crassa* [Case et al., *Proc. Natl. Acad. Sci. U.S.A.*, 76: 5259-5263 (1979)], and filamentous fungi such as, e.g., Neurospora, Penicillium, Tolypocladium [WO 91/00357 published 10 January 1991], and Aspergillus hosts such as *A. nidulans* [Ballance et al., *Biochem. Biophys. Res. Commun.*, 112: 284-289 (1983); Tilburn et al., *Gene*, 26: 205-221 (1983); Yelton et al., *Proc. Natl. Acad. Sci. U.S.A.*, 81: 1470-1474 (1984)] and *A. niger* [Kelly and Hynes, *EMBO J.*, 4: 475-479 (1985)].

Suitable host cells for the expression of glycosylated TSF receptor are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47-55 (1988); Miller et al., in *Genetic Engineering*, Setlow, J. K. et al., eds., Vol. 8 (Plenum Publishing, 1986), pp. 277-279; and Maeda et al., *Nature*, 315: 592-594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the TSF receptor DNA. During incubation of the plant cell culture with *A. tumefaciens*, the DNA encoding the TSF receptor is transferred to the plant cell host such that it is transfected, and will, under appropriate conditions, express the TSF receptor DNA. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published 21 June 1989.

However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.*, 36: 59 [1977]); baby hamster kidney cells (BHK, ATCC CCL 10); Chinese hamster ovary cells/-DHFR (CHO, Urlaub and Chasin, *Proc. Natl. Acad. Sci. U.S.A.*, 77: 4216 [1980]); mouse sertoli cells (TM4, Mather, *Biol. Reprod.*, 23: 243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383: 44-68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published 29 June 1989. In addition, plants may be transfected using ultrasound treatment as described in WO 91/00358 published 10 January 1991. For mammalian cells without such cell walls, the calcium phosphate precipitation method of Graham and van der Eb, *Virology*, 52: 456-457 (1978) is preferred. General aspects of mammalian cell host system transformations have been described by Axel in U.S. Pat. No. 4,399,216 issued 16 August 1983. Transformations into yeast are typically carried out according to the method of Van Solingen et al., *J. Bact.*, 130: 946 (1977) and Hsiao et al., *Proc. Natl. Acad. Sci. (U.S.A.)*, 76: 3829 (1979). However, other methods for introducing DNA into cells such as by nuclear injection, electroporation, or protoplast fusion may also be used.

E. Culturing the Host Cells

Prokaryotic cells used to produce the TSF receptor polypeptide of this invention are cultured in suitable media as described generally in Sambrook et al., supra.

The mammalian host cells used to produce the TSF receptor of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.* 59: 44 (1979), Barnes and Sato, *Anal. Biochem.*, 102: 255 (1980), U.S. Pat. Nos. 4,767,704; 4,657,866; 4,927,762; or 4,560,655; WO 90/03430; WO 87/00195; U.S. Pat. Re. 30,985; or copending U.S. Ser. No. 07/592,107 or 07/592,141, both filed in 3 October 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin TM drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. U.S.A.*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 (1980).

Antibodies useful for immunohistochemical staining and/or assay of sample fluids may be either monoclonal or polyclonal, and may be prepared in any mammal. Conveniently, the antibodies may be prepared against a native TSF receptor polypeptide or against a synthetic peptide based on the DNA sequences provided herein as described further in Section 3 below.

G. Purification of TSF Receptor Polypeptide

TSF receptor preferably is recovered from the culture medium as a secreted polypeptide, although it also may be recovered from host cell lysates when directly expressed without a secretory signal.

When TSF receptor is expressed in a recombinant cell other than one of human origin, the TSF receptor is completely free of proteins or polypeptides of human origin. However, it is necessary to purify TSF receptor from recombinant cell proteins or polypeptides to obtain preparations that are substantially homogeneous as to TSF receptor. As a first step, the culture medium or lysate is centrifuged to remove particulate cell debris. The membrane and soluble protein fractions are then separated. The TSF receptor may then be purified from the soluble protein fraction and from the membrane fraction of the culture lysate, depending on whether the TSF receptor is membrane bound. TSF receptor thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; ligand affinity chromatography, using, e.g., a TSF member as ligand, and protein A Sepharose columns to remove contaminants such as IgG.

TSF receptor variants in which residues have been deleted, inserted, or substituted are recovered in the same fashion as native TSF receptor, taking account of any substantial changes in properties occasioned by the variation. For example, preparation of a TSF receptor fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-TSF-receptor column can be employed to absorb the TSF receptor variant by binding it to at least one remaining immune epitope. Alternatively, the receptor molecule may be purified by affinity chromatography using a purified TSF member such as inhibin or activin as a ligand coupled to a (preferably) immobilized resin such as Affi-Gel 10 (Bio-Rad, Richmond, Calif.) or the like, by means well known in the art. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native TSF receptor may require modification to account for changes in the character of TSF receptor or its variants upon expression in recombinant cell culture.

H. Covalent Modifications of TSF Receptor Polypeptide

Covalent modifications of TSF receptor polypeptides are included within the scope of this invention. Both native TSF receptor and amino acid sequence variants of the TSF receptor may be covalently modified. One type of covalent modification included within the scope of this invention is a TSF receptor fragment. Variant TSF receptor fragments having up to about 40 amino acid residues may be conveniently prepared by chemical synthesis or by enzymatic or chemical cleavage of the full-length or variant TSF receptor polypeptide. Other types of covalent modifications of the TSF receptor or fragments thereof are introduced into the molecule by reacting targeted amino acid residues of the TSF receptor or fragments thereof with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking TSF receptor to a water-insoluble support matrix or surface for use in the method for purifying a TSF member such as activin or inhibin or anti-TSF-receptor antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group.

Another type of covalent modification of the TSF receptor polypeptide included within the scope of this invention comprises altering the native glycosylation pattern of the polypeptide. By altering is meant deleting one or more carbohydrate moieties found in native TSF receptor, and/or adding one or more glycosylation sites that are not present in the native TSF receptor.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the TSF receptor polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native TSF receptor sequence (for O-linked glycosylation sites). For ease, the TSF receptor amino acid sequence is preferably altered through changes at the DNA level, particularly by mutating the DNA encoding the TSF receptor polypeptide at preselected bases such that codons are generated that will translate into the desired amino acids. The DNA mutation(s) may be made using methods described above under the heading of "Amino Acid Sequence Variants of TSF Receptor Polypeptide."

Another means of increasing the number of carbohydrate moieties on the TSF receptor polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 September 1987, and in Aplin and Wriston, *CRC Crit. Rev. Biochem.*, pp. 259–306 (1981).

Removal of carbohydrate moieties present on the TSF receptor polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.*, 259: 52 (1987) and by Edge et al., *Anal. Biochem.*, 118: 131 (1981). Enzymatic cleavage of carbohydrate moieties on polypeptides can be achieved by the use of a variety of endo- and exo-glycosidases as described by Thotakura et al., *Meth. Enzymol.*, 138: 350 (1987).

Glycosylation at potential glycosylation sites may be prevented by the use of the compound tunicamycin as described by Duskin et al., *J. Biol. Chem.*, 257: 3105 (1982). Tunicamycin blocks the formation of protein-N-glycoside linkages.

Another type of covalent modification of TSF receptor comprises linking the TSF receptor polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

It will be appreciated that some screening of the recovered TSF receptor variant will be needed to select the optimal variant for binding to a TSF member and having the immunological and/or biological activity defined above. One can screen for stability in recombinant cell culture or in plasma (e.g., against proteolytic cleavage), high affinity to a TSF member, oxidative stability, ability to be secreted in elevated yields, and the like. For example, a change in the immunological character of the TSF receptor polypeptide, such as affinity for a given antibody, is measured by a competitive-type immunoassay. Other potential modifications of protein or polypeptide properties such as redox or thermal stability, hydrophobicity, or susceptibility to proteolytic degradation are assayed by methods well known in the art.

3. Uses of TSF Receptor Nucleic Acid, Polypeptide, and Antibodies Thereto

Nucleic acid encoding TSF receptor may be used as a diagnostic to determine the extent and rate of the expression of the TSF receptor in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule. Also, the TSF receptor nucleic acid can be used to detect nucleic acid encoding other TSF receptors. For example, such procedures as in situ hybridization, northern and Southern blotting, and PCR analysis may be used to determine whether DNA and/or RNA encoding a different TSF receptor is present in the cell type(s) being evaluated.

TSF receptor polypeptides are useful in radioreceptor assays to measure all bindable (presumably also active) forms of a TSF member such as inhibin or activin. If the TSF receptor is an inhibin receptor, such an assay would be specific for inhibin (i.e., activin would not be detected), and if the TSF receptor is an activin receptor, such an assay would be specific for activin (i.e., inhibin would not be detected). Such a radioreceptor assay would be conducted as described in the literature using the naturally purified or recombinant TSF receptor as the receptor element.

In addition, TSF receptor polypeptides are useful for screening for compounds that bind to them and have TSF biological activity as defined above. Preferably, these compounds are small molecules such as organic or peptide molecules that exhibit one or more of the desired activities of a TSF member such as inhibin or activin. Screening assays of this kind are conventional in the art, and any such screening procedure may be employed, whereby the test sample is contacted with the TSF receptor herein and the extent of binding and biological activity of the bound molecule are determined.

TSF receptor polypeptides are additionally useful in affinity purification of a TSF member or TSF-like molecules that bind to receptor (such as, for example, inhibin or activin or inhibin-like or activin-like molecules) and in purifying antibodies thereto. The receptor is typically coupled to an immobilized resin such as Affi-Gel 10 (Bio-Rad, Richmond, Calif.) or other such resins (support matrices) by means well known in the art. The resin is equilibrated in a buffer (such as one containing 25 mM TRIS, pH 7.5, 150 mM NaCl, and 0.1% O$\beta$G) and the preparation to be purified is placed in contact with the resin, whereby the molecules are selectively adsorbed to the receptor on the resin.

The resin is then sequentially washed with suitable buffers to remove non-adsorbed material, including unwanted contaminants, from the mixture to be purified, using, for an inhibin or activin mixture, e.g., 100 mM glycine, pH 3, and 0.1% octyl $\beta$-glucoside. The resin is then treated so as to elute the TSF member compound using a buffer that will break the bond between the TSF member compound and TSF receptor (using, e.g., 100 mM glycine, pH 3, and 0.1% octyl $\beta$ glucoside).

Therapeutic formulations of the receptor polypeptide for counteracting an excess amount of a TSF member are prepared for storage by mixing the receptor having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The receptor polypeptide to be used for in vivo administration must be sterile. This is readily accomplished by filtration through sterile filtration membranes, prior to or following lyophilization and reconstitution. The receptor polypeptide ordinarily will be stored in lyophilized form or in solution.

Therapeutic TSF receptor polypeptide compositions generally are placed into a container having a sterile access port, for example, an intravenous solution bag or vial having a stopper pierceable by a hypodermic injection needle.

The route of TSF receptor or receptor antibody administration is in accord with known methods, e.g., injection or infusion by intravenous, intraperitoneal, intracerebral, intramuscular, intraocular, intraarterial, or intralesional routes, or by sustained release systems as noted below. TSF receptor is administered continuously by infusion or by bolus injection. TSF receptor antibody is administered in the same fashion, or by administration into the blood stream or lymph.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.*, 15: 167–277 [1981] and Langer, *Chem. Tech.*, 12: 98–105 [1982] or poly(vinylalcohol)], polylactides (U.S. Pat. No. 3,773,919, EP 58,481), copolymers of L-glutamic acid and gamma ethyl-L-glutamate (Sidman et al., *Biopolymers*, 22: 547–556 [1983]), non-degradable ethylene-vinyl acetate (Langer et al., supra), degradable lactic acid-glycolic acid copolymers such as the Lupron Depot TM (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release TSF receptor compositions also include liposomally entrapped receptor. Liposomes containing receptor are prepared by methods known per se: DE 3,218,121; Epstein et al., *Proc. Natl. Acad. Sci. U.S.A.*, 72: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal receptor therapy.

An effective amount of TSF receptor to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily human dosage might range from about 1 μg/kg to up to 100 mg/kg or more, preferably 0.01 mg/kg to 1 mg/kg, depending on the factors mentioned above. Typically, the clinician will administer the receptor polypeptide until a dosage is reached that achieves the desired effect in blocking excess TSF member. The progress of this therapy is easily monitored by conventional assays.

The TSF receptor molecules of the present invention may also be used to induce the formation of anti-TSF-receptor antibodies, which are identified by routine screening. Such antibodies may either be polyclonal or monoclonal antibodies, or antigen binding fragments of such antibodies (such as, for example, F(ab) or F(ab)$_2$ fragments). Of particular significance to the invention are antibodies (and antigen-binding fragments of antibodies) that bind to any extracellular domain of the TSF receptor molecule. The most preferred anti-TSF-receptor antibodies (and antigen-binding fragments thereof) are those capable of preventing or inhibiting the binding of a TSF member to its receptor.

Polyclonal antibodies to the TSF receptor polypeptide generally are raised in animals by multiple subcutaneous (sc) or intraperitoneal (ip) injections of the TSF receptor polypeptide and an adjuvant. It may be useful to conjugate the TSF receptor polypeptide (including fragments containing the target amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or $R^1N=C=NR$, where R and $R^1$ are different alkyl groups.

The route and schedule of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant (or other suitable adjuvant) by subcutaneous injection at multiple sites. Seven to 14 days later animals are bled and the serum is assayed for anti-TSF receptor polypeptide titer. Animals are boosted until the titer plateaus. Preferably, the animal is boosted with the conjugate of the same TSF receptor polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering immune cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.,* 6: 511 (1976) and also described by Hammerling et al., In: *Monoclonal Antibodies and T-Cell Hybridomas,* Elsevier, N.Y., pp. 563-681 (1981) has been widely applied to produce hybrid cell lines that secrete high levels of monoclonal antibodies against many specific antigens.

It is possible to fuse cells of one species with another. However, it is preferable that the source of the immunized antibody-producing cells and the myeloma be from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the TSF receptor in test samples.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy,* Alan R. Liss, p. 77 [1985]). In fact, according to the invention, techniques developed for the production of chimeric antibodies (Morrison et al., *Proc. Natl. Acad. Sci.,* 81: 6851 [1984]; Neuberger et al., *Nature,* 312: 604 [1984]; Takeda et al., *Nature,* 314: 452 [1985]; EP 184,187; EP 171,496; EP 173,494; PCT WO 86/01533; Shaw et al., *J. Nat. Canc. Inst.,* 80: 1553-1559 [1988]; Morrison, *Science,* 229: 1202-1207 [1985]; and Oi et al., *BioTechniques,* 4: 214 [1986]) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

Techniques for creating recombinant DNA versions of the antigen-binding regions of antibody molecules (known as Fab fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed Fab protein to migrate to the periplasmic space (between the bacterial cell membrane and the cell wall) or to be secreted. One can rapidly generate and screen great numbers of functional Fab fragments for those that bind the antigen. Such TSF-receptor-binding molecules (Fab fragments with specificity for the TSF receptor polypeptide) are specifically encompassed within the term "antibody" as it is defined, discussed, and claimed herein.

In addition to their uses above, the TSF receptor polypeptides of the present invention are useful as the basis for assays of TSF member activity. Importantly, since such an assay measures a physiologically significant binding event, i.e., that of a hormone to its receptor, triggering a detectable change (such as phosphorylation, cleavage, chemical modification, etc.), it is likely to be both more sensitive and more accurate than immunoassays, which detect the physiologically non-significant binding of a TSF member to anti-TSF antibody. Moreover, the TSF receptor is capable of distinguishing its corresponding TSF member from other hormones with greater specificity than antibodies, which may cross-react with structurally similar molecules.

Although more sensitive and accurate than antibodies, the receptor molecules of the invention can be used to assay hormone levels in a sample in the same ways in which antibodies are used.

The anti-receptor antibodies of the present invention may also be used for diagnostic purposes, such as to measure the expression and function of a patient's TSF receptors. The anti-receptor antibodies also can be used in imaging to characterize tissue, or to define the presence and site of receptor-expressing cells.

For diagnostic purposes, the receptors and anti-receptor antibodies can be used in accordance with immunoassay technology. Examples of immunoassays are provided by Wide at pages 199-206 of *Radioimmune Assay Method,* Kirkham and Huner, ed., E & S. Livingstone, Edinburgh, 1970.

Thus, in one embodiment, TSF receptor molecules can be detectably labeled and incubated with a test sample containing TSF-member-like molecules (such as biological fluids, e.g., serum, sputum, urine, etc.), and the amount of receptor molecule bound to the sample is ascertained. In a second embodiment, antibody to the receptor, or to a TSF member, can be used to create a "pseudo-sandwich immunoassay." In one such assay (a "forward" assay) a sample suspected of containing a TSF member can be incubated in the presence of an immobilized anti-TSF antibody. Solubilized, detectably labeled TSF receptor molecules are added to the reaction mixture, and the amount of TSF member is determined by measuring the amount of bound receptor.

As will be evident to those of ordinary skill, various alternative assays can also be devised. The assay may be a simple "yes/no" assay to determine whether a TSF member is present or may be made quantitative by comparing the measure of labeled molecule with that obtained for a standard sample containing known quantities of the TSF member.

In another diagnostic test suitable for the receptor herein, "simultaneous" and "reverse" assays are used. A simultaneous assay involves a single incubation step as the antibody (or receptor) bound to the solid support and labeled receptor (or antibody) are both added to the sample being tested at the same time. After the incubation is completed, the solid support is washed to remove the residue of fluid sample and uncomplexed labeled antibody. The presence of labeled molecules associated with the solid support is then determined as it would be in a conventional sandwich assay.

In the "reverse" assay, stepwise addition first of a solution of labeled molecule (either receptor or antibody) to the fluid sample followed by the addition of unlabeled molecule (either antibody or receptor) bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then made as in the simultaneous forward assays.

The assay of this type requires that at least one binding partner be labeled with a reporter molecule. Examples of types of labels that can be used in the present invention include, but are not limited to, enzyme labels, radioisotopic labels, non-radioactive isotopic labels, fluorescent labels, toxin labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, e.g., horseradish peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^{111}$In, $^{32}$P, $^{14}$C, $^{125}$I, $^{3}$H, $^{131}$I, $^{35}$S, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, and the like. Examples of suitable non-radioisotopic labels include $^{157}$Gd, $^{55}$Mn, $^{52}$Tr, $^{56}$Fe, etc.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaladehyde label, a fluorescamine label, etc.

Examples of suitable toxin labels include diphtheria toxin, ricin, and cholera toxin. Examples of chemiluminscent labels include a luminal label, an isoluminal label, an aromatic acridinium ester label, an imidazole label, an acridinium salt label, an oxalate ester label, a luciferin label, a luciferase label, an aequorin label, and the like.

Those of ordinary skill in the art will know of other suitable labels that may be employed in accordance with the present invention. The binding of these labels to receptors, antibodies, or fragments thereof can be accomplished using standard techniques commonly known to those of ordinary skill in the art. For instance, coupling agents such as dialdehydes, carbodiimides, dimaleimides, bis-imidates, bis-diazotized benzidine, and the like may be used to tag the polypeptide with the above-described fluorescent, chemiluminescent, and enzyme labels. See, for example, U.S. Pat. Nos. 3,940,475 (fluorimetry) and 3,645,090 (enzymes); Hunter et al., *Nature*, 144: 945 (1962); David et al., *Biochemistry*, 13: 1014–1021 (1974); Pain et al., *J. Immunol. Methods*, 40: 219–230 (1981); Nygren, *J. Histochem. and Cytochem.*, 30: 407–412 (1982); O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147–166; Kennedy et al., *Clin. Chim. Acta*, 70: 1–31 (1976); and Schurs et al., *Clin. Chim. Acta*, 81: 1–40 (1977). Coupling techniques mentioned in the lattermost reference are the glutaraldehyde method, the periodate method, the dimaleimide method, and the m-maleimidobenzyl-N-hydroxysuccinimide ester method.

In the practice of the present invention, enzyme labels are a preferred embodiment. No single enzyme is ideal for use as a label in every conceivable assay. Instead, one must determine which enzyme is suitable for a particular assay system. Criteria important for the choice of enzymes are turnover number of the pure enzyme (the number of substrate molecules converted to product per enzyme site per unit of time), purity of the enzyme preparation, sensitivity of detection of its product, ease and speed of detection of the enzyme reaction, absence of interfering factors or of enzyme-like activity in the test fluid, stability of the enzyme and its conjugate, availability and cost of the enzyme and its conjugate, and the like. Included among the enzymes used as preferred labels in the assays of the present invention are alkaline phosphatase, horseradish peroxidase, beta-galactosidase, urease, glucose oxidase, glucoamylase, malate dehydrogenase, and glucose-6-phosphate dehydrogenase. Urease is among the more preferred enzyme labels, particularly because of chromogenic pH indicators that make its activity readily visible to the naked eye.

Immobilization of reagents is required for certain assay methods. Immobilization entails separating the TSF receptor from any analyte that remains free in solution. This conventionally is accomplished by either insolubilizing the receptor before the assay procedure, as by adsorption to a water-insoluble matrix or surface (Bennich et al., U.S. Pat. No. 3,720,760), by covalent coupling (for example, using glutaraldehyde cross-linking), or by insolubilizing the molecule afterward, e.g., by immunoprecipitation.

The foregoing are merely exemplary diagnostic assays for TSF members. Other methods now or hereafter developed for the determination of these analytes are included within the scope hereof.

The following examples are offered by way of illustration and not by way of limitation. The disclosures of all literature references cited in the specification are expressly incorporated herein by reference.

EXAMPLE I

Purification of Bovine Inhibin/Activin Receptor

A. General Membrane Extract (ME) Procedure

Bovine pituitaries (in an amount of 200 g unless otherwise indicated) were suspended in 150 mM NaCl (latter ME had protease inhibitor cocktail added, which comprised 1 mM EDTA, 25 µg/ml aprotinin, 0.5 µg/ml leupeptin, and 0.7 µg/ml pepstatin), disrupted in a blender, and subsequently mixed with a stir bar at 5° C. for one hour. The mixture was then sedimented at 10,000×g to remove particulate matter. The resulting supernatant was centrifuged at 105,000×g for 3 hours. The ultracentrifugation pellet was resuspended in 85 mM TRIS, pH 7.8, 0.1% octyl β glucoside (OβG), 30 mM NaCl, 1 mM EDTA, and 25 µg/ml aprotinin.

Several MEs were prepared separately by this procedure, numbered in the order of their preparation from ME1 to ME9. For ME preparations 3-9, the supernatant was treated with DNase (Boehringer Mannheim) overnight at 1 unit/μg DNA to reduce viscosity and improve sedimentation of particulate matter during ultracentrifugation. DNase-treated samples were sedimented at 105,000×g for 3 hours and clear red supernatants were found. For ME preparations 4-9, 0.5 μg/ml leupeptin and 0.7 μg/ml pepstatin were also added. The resulting suspension was sedimented at 105,000×g.

B. FITC-Conjugated Inhibin

The pH of recombinant human inhibin (Mason, U.S. Pat. No. 4,798,885, supra) was adjusted to 8.0 with 1M $Na_2CO_3$, pH 9.3. A total of 7 mg of fluorescein isothiocyanate (FITC, Sigma) was added to 140 μl dimethyl formamide (DMF) and subsequently diluted in water to a final concentration of 1 μg/μl. A total of 2 μg of this FITC solution was added to 10 μg of the inhibin to give a total volume of 100 μl. After exactly one hour of end-over-end mixing, the sample was sedimented in a microcentrifuge to remove particulate matter (14,000 rpm for 15 min.). Free FITC was removed from the sample by diafiltration using a 10-Kd molecular weight cut-off ultrafiltration (UF) membrane (Ultrafree-MC Filter Unit, Millipore). Conjugated inhibin was used on the day of preparation. If the analysis was to be carried over to the following day, the conjugated hormone was stored at −70° C.

C. Size-Exclusion Chromatography of ME Incubated with FITC-Conjugated Inhibin A Perkin-Elmer fluorescence detector was connected to a Hewlett Packard HP 1090 HPLC (excitation 480 nm, emission 525 nm). A chart recorder or an integrator was used to monitor the fluorescent peaks. 50 μl of ME1 was added to 140 μl of elution buffer (100 mM $PO_4$, pH 6.0±0.1, and 0.1% OβG) with 5-10 μl of inhibin-FITC (assuming 100% recovery of FITC-labeled inhibin; [hormone]=0.7 μg/μl). After a 30-min. incubation at ambient temperature, 50 μl of sample was loaded. The TSK 3000 SWXL size-exclusion column with guard column was eluted with the elution buffer described above using a flow rate of 1 ml/min.

Inhibin-FITC eluted at a molecular weight less than expected (27 Kd vs. 32 Kd) relative to the gel filtration standards (Sigma), suggesting some interaction with the TSK gel. This observation was also seen with unlabeled inhibin, indicating that the FITC tag was not responsible for the delay in retention time. A fluorescent peak was observed at a molecular weight greater than 200 Kd (i.e., near the void), suggesting that there was a protein(s) in the ME that bound to inhibin-FITC. Fluorescent peaks were collected and analyzed using SDS-PAGE. Many proteins co-eluted in the 200 Kd+ peak. Furthermore, there was no detectable inhibin-FITC band observed on the gels (maximum recoverable inhibin-FITC=0.7 μg/μl × 10 μl=7 μg).

D. SDS-PAGE Analysis

For all SDS-PAGE analyses conducted the following conditions were employed unless otherwise indicated. Ten percent acrylamide SDS-PAGE was used. If the PAGE was reduced, the reducing agent was 5% β-mercaptoethanol. The percent SDS of the sample buffer was 2%. The molecular weight markers employed were myosin (200,000), *E. coli* β-galactosidase (116,250), rabbit muscle phosphorylase b (97,400), bovine serum albumin (66,200), and hen egg white ovalbumin (42,699). The molecular weights were determined by plotting log molecular weight versus molecular weight marker migration. Silver staining was employed except when indicated otherwise.

E. Ligand Affinity Chromatography Columns in General

Four support matrices were utilized to immobilize a biologically active (in the rat pituitary FSH-release assay) form of recombinant inhibin A (as described by Mason, U.S. Pat. No. 4,798,885, supra) that was proteolytically clipped at amino acid 14 to 18 during production and/or isolation. All resins utilized a spacer arm to prevent steric hindrance from interfering with the isolation of receptor. Inhibin A in ~30% acetonitrile, 0.1% trifluoroacetic acid, pH ~3, was concentrated from 0.1 to 1 mg/ml using a stirred cell with YM 10 UF membrane (Amicon). The pH was rapidly increased to 5 or 8, depending on the support resin, with 1M citrate, pH 5 or 1M TRIS, pH 8, respectively. Subsequently, inhibin A was buffer exchanged into coupling buffer (0.1M citrate buffer, pH 5, or 0.1M sodium bicarbonate, pH 8) according to manufacturer's protocol using gel filtration PD 10 columns (Pharmacia).

1. Affi Prep 10 Support Matrix

About 9 mg inhibin A was immobilized to 3 ml of Affi Prep 10 support matrix as recommended by its manufacturer, BioRad. This resin was used once before switching to Affi Gel 10. Affi Prep 10 (hydrophilic polymer) and Affi Gel 10 (crosslinked agarose) share the same spacer arm (10 atoms) and coupling chemistry (N-hydroxysuccinimide displaced > stable amide bond formed) through the free amino groups of the inhibin.

2. Affi Gel 10

Two batches of inhibin A coupled to Affi Gel 10 were prepared as directed by BioRad (9 mg inhibin coupled to 3 ml Affi Gel per batch, carbonate coupling buffer). TRIS was also immobilized to Affi Gel to prepare precolumns for reducing non-specific adsorption to the affinity column support. Five mg of human recombinant activin A (Mason, U.S. Pat. No. 4,798,885, supra) was also immobilized to ~3 ml of Affi Gel 10.

3. Affi Gel HZ

Affi Gel HZ was used to immobilize inhibin A through the carbohydrate groups of the alpha chain. The procedure described by BioRad was used to couple the ligand to the support.

4. HiPAC

A silica-based support with activated aldehyde groups was used to immobilize inhibin A through the primary amino groups (ChromatoChem).

F. Isolation of Inhibin/Activin Receptor Using Ligand Affinity Chromatography

1. Ligand Affinity Chromatography 1

ME2 (cloudy) was loaded on an Affi Prep/inhibin column. The affinity column was extensively washed with 10 mM TRIS, pH 7.5, and 0.1% OβG. After a stable $A_{280}$ baseline was achieved, proteins were eluted from the affinity column with 100 mM acetic acid, pH 3, and 0.1% OβG. Eluent was immediately neutralized with 3 M TRIS, pH 8.5, and stored at 5° C.

SDS-PAGE Analysis

SDS-PAGE analysis revealed that the eluent contained ligand as well as many other proteins. Consequently, direct sequencing of the eluent was difficult.

N-Terminal Sequence Analysis

The strongest amino acid sequence signal found for a protein bound to a 2-cm, 15-μm in diameter C4 reverse phase column was that of the β chain of hemoglobin.

Three significant changes were subsequently made in the ligand affinity column procedures. Further recoveries used Affi Gel 10 as the support gel (a frequently used resin in several papers describing the isolation of receptors). In addition, a more stringent wash buffer with 150 mM NaCl as well as a precolumn were incorporated into the procedure to reduce non-specific protein binding.

2. Ligand Affinity Chromatography 2

ME3 was loaded on an Affi Gel-Tris precolumn (BV=1 ml) and subsequently through an Affi Gel-inhibin affinity column (BV=3 ml, 3 mg inhibin/ml resin, run in series after the precolumn). The affinity column was extensively washed with 25 mM TRIS, pH 7.5, 150 mM NaCl, and 0.1% OβG. The putative receptor was then eluted with 100 mM glycine, pH 3, and 0.1% OβG. Eluent (~5 ml) was immediately neutralized with 1M NaOH and stored at ~20° C. Incubation of FITC-labeled inhibin with the flow-through ME fraction and subsequent size-exclusion chromatography analysis indicated that there was potentially more receptor remaining. As a result, the flow-through fraction was diluted ¼ with 100 mM PO₄, pH 6, and 0.1% OβG (final volume=9.5 ml), filtered and recirculated for 45 min. (flow rate =3 ml/min.) over the inhibin column. After a 40-min. wash, the column was eluted (~5 ml). SDS-PAGE indicated that the proteins found in the initial purification were identical to those recovered from the flow-through.

SDS-PAGE Analysis of Flow-Through Fraction Eluent

The eluent contained three major proteins as determined by a non-reduced SDS-PAGE gel. The molecular weights of the three proteins were approximately 32 Kd (inhibin from ligand affinity column), 60 Kd, and over 200 Kd. Upon reduction with mercaptoethanol, the 200 Kd+protein band migrated to ~150 Kd.

N-Terminal Sequence Analysis

Flow-through fraction eluent was loaded on a C4 reverse phase HPLC column (15 μm bead diameter, column height 20 mm, n-propanol/TFA linear gradient). Peaks at approximately 11, 19, and 23 min. were determined to be an artifact, inhibin, and the potential receptor, respectively, by reduced SDS-PAGE. No detectable amino acids were found in the sequencing of the material remaining on the C4 column, suggesting that all of the proteins had been eluted. The background of the sequencing chromatograms was stable with successive cycles, suggesting that there were no N-terminal blocked proteins on the C4 column. The C4-isolated potential receptor did not yield an amino acid sequence, suggesting that there was insufficient protein for detection.

3. Ligand Affinity Chromatography 3

To recover more receptor, 500 instead of 200 g of bovine pituitaries was prepared for ME4. (Unless noted otherwise, all subsequent MEs were derived from 500 g of pituitaries.) ME4 was loaded on an Affi Gel-10.TRIS column (bed volume (BV)=1 ml), an inhibin A column immobilized through the carbohydrate groups (Affi Gel-HZ, 3-ml BV, 9 mg inhibin), and finally through an inhibin A column immobilized through the free amino groups (Affi Gel-10, 3-ml BV, 9 mg inhibin). The affinity columns were extensively washed with 25 mM TRIS, pH 7.5, 150 mM NaCl, and 0.1% OβG. The putative receptor was then eluted with 100 mM glycine, pH 3, and 0.1% OμG from both inhibin columns separately. The eluents (~5 ml) were immediately neutralized with 3M TRIS, pH 8. Only ~25 of the 45 ml of ME4 was passed through the columns because of particulate matter fouling the precolumn. Upon further investigation, it was found that ME4 was viscous due to DNA that retarded the sedimentation of particles. The remaining 20 ml was treated with DNase according to manufacturer's instructions at 5° C. (Boehringer Mannheim). The solution was diluted with wash buffer to 35 ml, centrifuged at 105,000×g for 1.5 hours, and then loaded on the columns (new precolumn). No plugging of the precolumn was observed. [There were large pellets at the bottom of the ultracentrifugation tubes after DNase treatment.] The 35-ml sample was recirculated through the columns for 30 minutes. After a 60-minute wash, the columns were eluted separately. The eluents were immediately neutralized and stored at −20 C.

SDS-PAGE Analysis

Using reduced SDS-PAGE, it was determined that the 150-Kd protein thought to be the inhibin receptor was present in the Affi Gel-10 inhibin eluent, but it was absent in the Affi Gel HZ-inhibin eluent. This result suggests that the orientation of inhibin immobilized through the carbohydrate group prevented the binding of the putative receptor to the ligand. The high-molecular-weight protein thought to be the inhibin receptor apparently did not elute from the reverse phase C4 column at the same retention time as was observed with ME3. This might be the result of the additional protease inhibitors added to ME4, the use of a different batch of bovine pituitaries, or the storage of the sample at −20° C. immediately after elution.

N-Terminal Sequence Analysis

The N-terminal sequence of a protein bound to the C4 column was valine connected to leucine connected to serine, histidine, or cysteine, followed by glutamic acid. This sequence was observed for both the DNase-treated and untreated ME. Over fifty proteins were found in the Dayhoff protein database for each of the three potential 4-amino-acid N-terminal sequences (i.e., 4 amino acids are insufficient for protein identification).

4. Ligand Affinity Chromatography 4

ME5 was passed through an Affi Gel-10-TRIS column (BV=2 ml), and two inhibin columns connected in series (3-ml BV/each, started at 9 mg inhibin/each). Columns were extensively washed with 25 mM TRIS, pH 7.5, 150 mM NaCl, and 0.1% OβG. The putative receptor was then eluted with 100 mM glycine, pH 3, and 0.1% OβG. The flow-through fraction as well as the residual supernatant that was remaining after the final ultracentrifugation (~5 ml of sample that was cloudy in appearance, so it was not incorporated into the first ME sample) was reprocessed over the columns. A final third reprocessing recovery was also performed. All eluents were immediately neutralized with 3M TRIS, pH 8, and stored at −20° C.

SDS-PAGE and N-Terminal Sequence Analysis

Using RP-HPLC (15-μm bead diameter C4 resin in a 2-cm column, 0-70% n-propanol/TFA gradient) the receptor was concentrated and purified to homogeneity. The receptor-enriched RP fractions were run on reduced 10% SDS-PAGE, transferred to PVDF, and stained with Coomassie blue.

The single protein band at about 150 Kd believed to be the inhibin receptor was cut out of the transblot and sequenced. The N-terminal sequence was found to be:

ValLeuThrGluGluThrGluIleIleMetProThrProLys-ProGluLeuXaaAlaXaaXaaAsn (Sequence Identity No. 1).

There is a proteolytic clip site between the initial Val-LeuThr and the remainder of the sequence. The Xaa residues indicate unknown amino acids. The clip site provided confirmation of the amino acids in the sequence (i.e., the same amino acid came up three cycles later).

5. Ligand Affinity Chromatography 5

ME6 was passed through a TRIS column (Affi Gel-10, BV=1 ml) and an inhibin column (Affi Gel-10, 6-ml BV, started at 18 mg inhibin). The affinity column was thoroughly washed (45 BV) using a wash buffer of 25 mM TRIS, pH 7.5, 150 mM NaCl, and 0.1% OβG. The putative receptor was acid eluted with 100 mM glycine, pH 3, and 0.1% OβG. The flow-through fraction was reprocessed over the column. All eluents were immediately neutralized with 1M TRIS, pH 8, and stored at −20° C.

SDS-PAGE and N-Terminal Sequence Analysis

Ten percent of the eluents were used to determine the recovery yield of RP-HPLC (~40% recovery). Seventy percent was used to confirm the sequence of the 150-Kd protein by running on reduced SDS-PAGE, transferring to PVDF, and staining with Coomassie blue. The sequence for dimerized bovine serum albumin was found at ~150 Kd on the transblot from the reduced SDS gel. Unlike before, there was no RP-HPLC step to enrich for the putative receptor. Instead, the eluent sample was dialyzed against 10 mM TRIS, pH 7.5 and 0.1% OβG, dried down, run on SDS-PAGE, and transblotted to PVDF. This suggests that the N-terminus of the inhibin receptor was blocked, that the RP-HPLC step is required to obtain sequence, or that the wrong band was cut out of the PVDF (there did appear to be another faint band just above the one that was cut out).

6. Ligand Affinity Chromatography 6

150 g of bovine pituitaries were used in preparing ME7. The 25 ml of ME was diluted to 40 ml with wash buffer. The diluted ME was divided into 4×10-ml samples. Ten ml of ME was loaded on the affinity column (BV=6 ml). The column was washed for 1.5 hours with 25 mM TRIS, pH 7.5, 150 mM NaCl, and 0.1% OβG (flow rate=3 ml/min). The putative receptor was then eluted with 100 mM glycine, pH 3, and 0.1% OβG. The eluent was immediately neutralized with 3M TRIS. The flow-through fraction was also reloaded, and treated as above. The TRIS precolumn from this procedure was also washed and eluted for gel analysis.

A 50-ml sample of 0.1 mg/ml inhibin was concentrated to ~2 ml using a YM-10 ultrafiltration membrane in an Amicon stirred cell. The concentrated sample was neutralized with 1M TRIS, pH 8 (~100 μl) and added to 10 ml of ME. After a 3-hour incubation, the ME was loaded on the affinity column. The wash and elution conditions were identical to what was described above (new TRIS precolumn was used). The flow-through fraction was also loaded, and treated as above.

Ten ml of ME7 was extensively dialyzed against the wash buffer and then acidified to pH 3. Subsequently, the ME7 was filtered through a 100-Kd MWCO membrane (Ultrafree-MC Filter Unit, Millipore). The filtrate was assayed for inhibin and activin in the respective ELISAs.

Observations

The addition of free inhibin into the ME prior to loading on the immobilized inhibin column greatly reduced the recovery of the putative receptor.

No detectable inhibin (<0.7 ng/ml) or activin (<0.5 ng/ml) was measured in the acid-treated ME passed through a 100-Kd ultrafiltration membrane, suggesting that the inhibin observed in the eluent results from the affinity column and not from the ME.

7. Ligand Affinity Chromatography 7

ME8 (125-g preparation from bovine pituitaries) was loaded on a TRIS column (BV=1 ml), an inhibin column (Affi Gel-10, 6-ml BV, started at 18 mg inhibin), and finally an activin column (Affi Gel-10, 3-ml BV, 5 mg activin). Affinity columns were extensively washed for 90 minutes at a flow rate of 3 ml/min with 25 mM TRIS, pH 7.5, 150 mM NaCl, and 0.1% OβG. Columns were individually eluted with 100 mM glycine, pH 3, and 0.1% OβG. The flow-through fraction was reprocessed. All eluents were immediately neutralized with 1M TRIS, pH 7.5, and stored at −20° C.

The remaining ME8 (I25-g preparation of bovine pituitaries) was used to evaluate inhibin immobilized to a silica-based HPLC column (ChromatoChem).

| HPLC Time Table | | | |
|---|---|---|---|
| Time (min.) | % A | % B | Flow Rate (ml/min.) |
| 0 | 100 | 0 | 2 |
| 25 | 0 | 100 | 2 |
| 25.01 | 100 | 0 | 2 |
| 35 | 100 | 0 | 2 |

Buffer A: 10 mM PO$_4$, pH 6.8, 100 mM Na$_2$SO$_4$ and 0.1% OβG.
Buffer B: 10 mM PO$_4$, pH 2.5, 100 mM Na$_2$SO$_4$ and 0.1% OβG.
2 ml of ME8 was loaded onto the 0.83 ml BV column per run (n = 2).
1 ml fractions were collected throughout the isolation procedure.
Fractions that had a pH < 5 were characterized by SDS-PAGE.

SDS-PAGE Analysis

The eluents from the immobilized activin and inhibin columns both had a single protein band at 135-150 Kd, depending on the size of the gel, by silver stain on reduced SDS-PAGE. The molecular weight was 135 Kd using a 8×10 cm gel and was 148 Kd using a 12×15 cm gel.

N-Terminal Sequence Analysis

For the Affi Gel columns, more putative receptor protein was found in the activin eluent that in the inhibin column eluent. N-terminal sequencing of the 135-150-Kd band on transblots revealed that the first 15-20 amino acids were identical for the inhibin and activin column eluents. These data also confirmed the previous sequence observed from Ligand Affinity Chromatography 4. Twenty percent of the inhibin eluent was clipped at the valine-leucine-threonine and glutamic acid-glutamic acid juncture and 50% of the activin column eluent was clipped at the same position. The RP-HPLC profiles for the inhibin and activin column eluents were also similar.

In addition to the Dayhoff protein database that suggested that the 135-150-Kd band was an unknown protein, a larger Genbank DNA database also indicated a novel sequence. Another major protein band at 80 Kd (reduced SDS-PAGE) was found to have the sequence:

AlaValAsnProThrGlyArgAspAlaValGlu-
ProValAlaValXaa(Ala)LeuAspLeuIleAsnLys
(Sequence Identity No. 2), where Xaa is an unknown amino acid and the Ala in parenthesis is believed to be correct. This sequence was found also to be absent from the databases. The protein was not affected in the competition studies, suggesting some non-specific interaction with columns.

The activin column eluent that had been transferred to PVDF and sequenced for ~20 cycles was digested with cyanogen bromide. The resulting digest was sequenced and 3-5 peptide sequences were observed, suggesting either that the number of methionines was low or that the protein was highly glycosylated. The sequence occurring after the methionine at position 10 was not found, indicating that the N-terminus for the activin receptor was not blocked.

The inhibin-HiPAC column was found to improve greatly the receptor recovery yield based on SDS-PAGE while reducing purification time from ~2.5 hours to 35 mins. The 80-Kd protein was also observed in the inhibin-HiPAC eluent. The eluent fractions from the HPLC column were those used to confirm the N-terminal sequence of the inhibin receptor (no RP-HPLC step prior to sequencing).

8. Ligand Affinity Chromatography 8

ME9 (equivalent to 125 g of bovine pituitaries) was passed through a TRIS column and an activin column. Columns were extensively washed (45 BV) with 25 mM TRIS, pH 7.5, 150 mM NaCl, and 0.1% O$\beta$G. Putative activin receptor was then eluted with 100 mM glycine, pH 3, and 0.1% O$\beta$G. The flow-through fraction was reprocessed over the column. All eluents were immediately neutralized with 1M TRIS, pH 7.5, and stored at $-20°$ C.

The remaining ME (125 g bovine pituitaries) was divided into four fractions: a control, a 60°-70° C. heat denaturation (not examined since protein precipitation formed in ~15 min.), a 2-mg inhibin spike-back, and a 100-Kd ultrafiltration/diafiltration fraction (i.e., 5 ml of ME diluted into 250 ml of low-pressure wash buffer and concentrated to ~5 ml with 100 Kd Amicon UF membrane). These so-treated ME mixtures were purified using the inhibin-HiPAC HPLC system.

| HPLC Time Table | | | |
|---|---|---|---|
| Time (min.) | % A | % B | Flow Rate (ml/min.) |
| 0 | 100 | 0 | 1 at 5 min. 2 ml/min. |
| 20 | 100 | 0 | 2 |
| 25 | 0 | 100 | 2 |
| 25.01 | 100 | 0 | 2 |
| 35 | 100 | 0 | 2 |

Buffer A: 10 mM PO$_4$, pH 6.8, 100 mM Na$_2$SO$_4$ and 0.1% O$\beta$G.
Buffer B: 10 mM PO$_4$, pH 2.5, 100 mM Na$_2$SO$_4$ and 0.1% O$\beta$G.
5 ml of ME9 was loaded onto the 0.83 ml BV column.
2 ml column fractions were collected throughout the run.

Analysis

Activin-Affi Gel Column

Most of the activin column eluents, both initial and reprocessed, were used to determine internal sequence.

Inhibin-HiPAC Column

There were few proteins in the wash buffer just prior to the elution of putative inhibin receptor. A majority of the putative receptor was eluted in the first 5 BV of elution buffer. Reprocessing the flow-through fraction in this system yielded less receptor than what had been observed using the inhibin-Affi Gel column. That is, the HiPAC column even with less ligand bound was more efficient in recovering the alleged receptor than the Affi Gel column. The UF/DF procedure to reduce the number of contaminating proteins in the eluent was not effective and in fact reduced the recovery of the inhibin receptor. The addition of 2 mg inhibin to the ME greatly reduced the recovery of the 135-150-Kd protein (reduced SDS-PAGE).

G. Cyanogen Bromide Digestion of Activin Receptor for Determining Internal Sequence The activin column eluent from ligand affinity chromatography 8 described above was subjected to analysis by reduced SDS-PAGE under the conditions described above. The gel results were that the major protein in the eluent Was the 135-150-Kd protein, which is the putative receptor. As a result, the major sequence observed after the cyanogen bromide digest should be that of the receptor. The activin column eluent was treated with dithiothreitol for one hour at 40° C. to reduce oxidized methionine (oxidized methionine is not cleaved by cyanogen bromide). The reduced sample was then incubated with cyanogen bromide overnight at room temperature using standard procedures as described, e.g., in Spande et al., *Adv. Protein Chem.*, 24: 97 (1970) and Gross and Witkop, *J. Biol. Chem.*, 237: 1856 (1962). The peptides resulting from the digest were separated using RP-HPLC (2-cm C4 column) with a propanol/TFA linear gradient (0-70%). The amino acid sequence of the peptides in the RP-HPLC fractions was determined.

Two potential internal sequences were identified:
1) MetTyrAlaProGluTyr (Sequence Identity No. 3)
2) MetIlePheAlaLeuLeuPhePheGly (Sequence Identity No. 4)

H. Rat Germ Cell Competition Assay

Inhibin A and activin A as described above with and without FITC label were diluted in an elution buffer of 100 mM phosphate, pH 6.0, 0.1% (w/v) SDS in the presence and absence of 21 mM dithiothreitol, and subsequently heated to 100° C. for 5 min. Approximately 100 ng of denatured hormone was injected on a TSK 3000 SWXL column using an HP 1090 high-performance liquid chromatography system (Hewlett Packard). The column was eluted with the same elution buffer using a flow rate of 0.5 ml/min. Peaks were monitored with a fluorescence detector (excitation 480 nm, emission 525 nm). Molecular weights were determined for the hormones by plotting log molecular weight for the gel filtration standards (Sigma): albumin (66 Kd), carbonic anhydrase (29 Kd), and cytochrome C (12.4 Kd) as a function of elution volume/void volume (Ve/Vo).

The size-exclusion chromatography is shown in FIG. 2. No autofluorescence was observed for the unlabeled proteins. For the FITC-conjugated proteins, only mature inhibin and activin peaks were present, indicating the absence of protein contaminants, hormone precursors, and SDS-stable aggregates. Calculated molecular weights for inhibin A and activin A were 27 Kd (actual 32 Kd) and 28 Kd (actual 28 Kd), respectively. Upon reduction with dithiothreitol (DTT), the elution of the inhibin $\alpha$ chain (18 Kd) was found to be retarded relative to the $\beta_A$ chain (14 Kd), suggesting that the discrepancy in the actual and calculated molecular weights for inhibin resulted from the $\alpha$ chain adsorbing to the size-exclusion gel. Peak areas for the $\alpha$ and $\beta$ chains of inhibin suggest a FITC conjugation ratio of 1:2 (maximum theoretical ratio 2:9).

FITC-labeling of inhibin, activin, and ovalbumin (background) was performed as described by Woodruff et al., in *Methods in Enzymology: Growth Factors, part C*, Barnes, D., Mather, J., Sato, G. (eds), Academic Press, San Diego, Calif., 198: 347–356 (1991), with the modifications as described by Chatelier et al., *EMBO J.*, 5: 1181–1186 (1986). Briefly, 10 μg of inhibin A. activin A, activin B, or ovalbumin was mixed with 1 μg FITC and allowed to react for one hour at room temperature. Unconjugated FITC was removed from the reaction by diafiltration. Conjugated hormone was analyzed by size-exclusion chromatography. Bioactivity was measured using a rat pituitary bioassay.

Thirty-one-day-old male Sprague-Dawley rats (Charles River Laboratories, Wilmington, Mass.) were sacrificed by carbon dioxide asphyxiation. The testes of these rats were removed and placed directly into DMEM:F12 (1:1) medium with HEPES and gentamycin (50 μg/ml). The testes were decapsulated and the interstitial tissue was lysed with solution A [1M glycine, 2 mM EDTA, 20 IU/ml DNase I (Boehringer-Mannheim) and 0.01% soy trypsin inhibitor (STI) (Gibco) in $Ca^{+2}Mg^{+2}$-free PBS, pH 7.2] and the tissue was exposed briefly (5–10 min) to collagenase-dispase [in Dulbecco's Modified Eagle's/Ham's F12 nutrient mixture (1:1 v/v) (Gibco) supplemented with 1.2 g/l sodium bicarbonate, 10 mM HEPES buffer, 20 mg/l gentamycin sulfate, and 1 mg/ml bovine serum albumin]. Tubules were minced with scissors to 1–3 mm pieces and passed 3–4 times through an 18-gauge needle using a sterile syringe. The suspension was washed by centrifugation and resuspended in fresh medium. Clumps of Sertoli cells were trapped in a 20-μM Nytex TM nylon mesh with the single cells (germ cells) passing through. Germ cells were freed of debris by repeated washing (4–6 times) in medium. The enriched germ cell preparation was cultured overnight in primary testes cell medium [15 mM Dulbecco's Modified Eagle's/Ham's F12 nutrient mixture (1:1 v/v) (Gibco) supplemented with 1.2 g/l sodium bicarbonate, 10 mM HEPES buffer, 20 mg/l gentamycin sulfate, 5 μg/ml insulin (Sigma, St. Louis, MO), 5 ng/ml human transferrin (Sigma), 5 ng/ml epidermal growth factor (Sigma), 5 ng/ml $\alpha$-tocopherol (Sigma), and 25 μg/ml aprotinin (Miles Laboratories, Naperville, Ill.)] plus Sertoli cell-conditioned medium (2:1, v/v), prepared by collecting the conditioned media from Sertoli and germ co-cultures of 10-, 15-, 20-, and 26-day-old rat testes decapsulated and processed as described by Mather and Philips, in *Methods in Molecular and Cell Biology*, Barnes et al., eds., Alan R. Liss, Inc. (New York, 1984), pp. 29–45, followed by 48 hours of culture in the primary testes cell medium described above.

Binding was performed using $1 \times 10^5$ of the above-described rat germ cells suspended in binding medium [Dulbecco's Modified Eagle's/Ham's F12 nutrient mixture (1:1 v/v) (Gibco) supplemented with 1.2 g/l sodium bicarbonate, 10 mM HEPES buffer, 20 mg/l gentamycin sulfate, and 1 mg/ml bovine serum albumin] with FITC-labeled inhibin A, FITC-labeled activin A, or FITC-labeled activin B (as in Mason, U.S. Pat. No. 4,798,885, supra). Following incubation at 4° C. for 30 minutes the cells plus bound ligand were washed twice with PBS-BSA. Non-specific binding was determined in the presence of 1000-fold excess unconjugated ligand. Binding is reported as fluorescent intensity per cell population minus background fluorescence divided by the percent number of cells per population and corrected for percent competition. Within each experiment duplicate or triplicate analysis of binding was performed. Many independent binding experiments were completed.

Figure 3A:
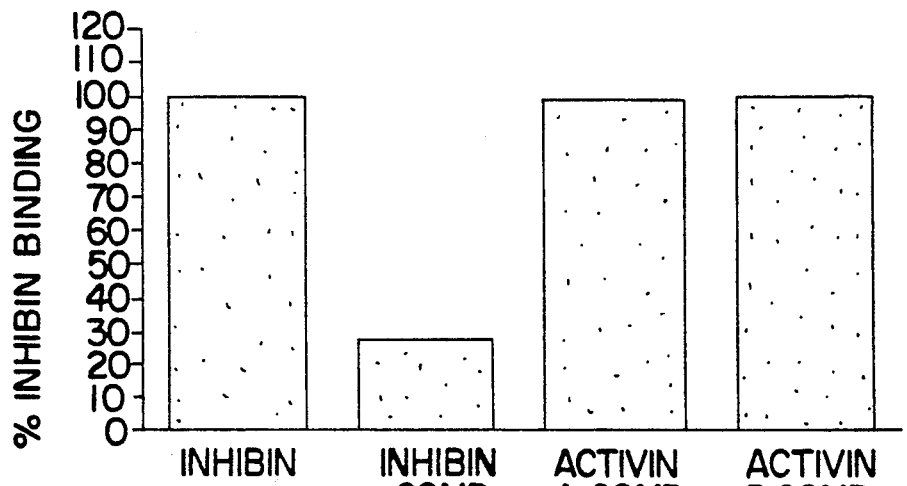
FIG. 3 shows competition of inhibin A (FIG. 3A), activin A (FIG. 3B), and activin B (FIG. 3C) for heterologous receptors, where the inhibin and activins are conjugated to FITC and bound to cells from a 31-day germ cell co-culture. Competition was in the presence of 1000-times excess of the respective hormone. Total mean fluorescence for the population minus background was calculated in each case.
Figure 3B:
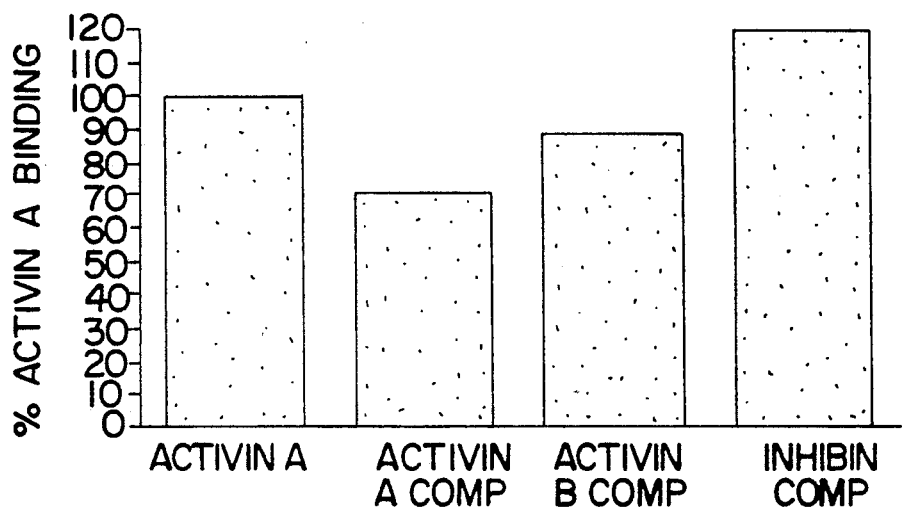
Figure 3C:
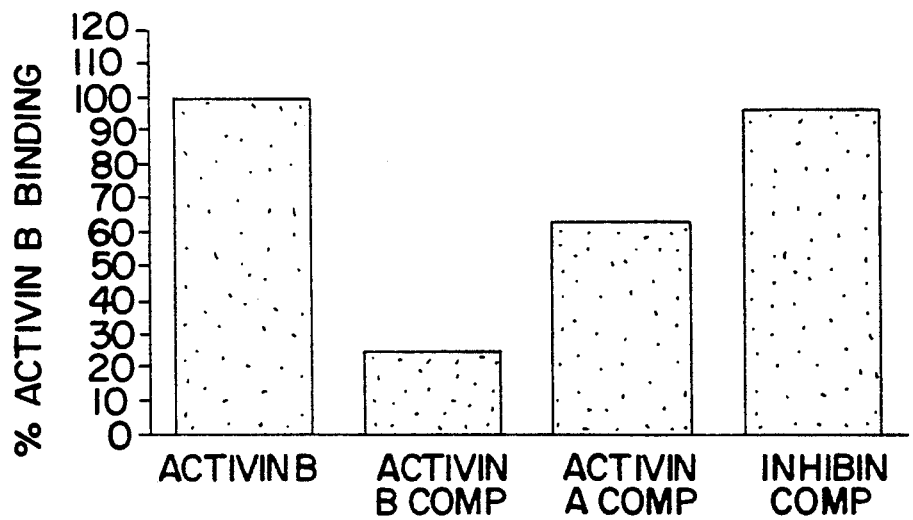

FIG. 3 shows the percent competition based on relative fluorescence generated by co-incubations with 1000-fold excess of non-labeled hormone. Surface binding by inhibin A-FITC was competed by unlabeled inhibin A, but not by activin A or activin B. Activin B demonstrated a similar pattern of complete competition in the presence of unlabeled activin B. Activin A was partially competed by activin B and activin A when analyzed for the total germ cell population. Inhibin A did not bind to either of the activin receptors. Inhibin B and activin AB were not tested; it is possible that independent receptors for these species also exist. TGF-$\beta$ did not compete with inhibin or activin binding. When binding was assessed for individual germ cell stages, similar binding by inhibin A and activin A was found with one exception: activin A did not bind leptotene-/zygotene primary spermatocytes.

I. Conclusions

There are two separate receptors for activin(s) and inhibin(s) based on the following experimental data obtained:

1) No cross-competition in binding of FITC-activin A by inhibin A and vice-versa in rat germ cell assay.

2) Immobilized inhibin A binds a protein that is competed with free inhibin A added to the O$\beta$G soluble pituitary membrane extract.

3) Immobilized activin A binds a protein that is competed by activin A but not inhibin A.

4) Early pachytene spermatocytes bind inhibin but not activin. Most cells bind both.

The activin and inhibin receptors are related, as indicated by the fact that they have the same N-terminal amino acid sequence (ValLeuThrGluGluThrGluIleIleMetProThrProLysProGluLeuXaaAlaXaaXaaAsn, which is Sequence Identity No. 1) and they are similar in size (135-150-Kd single band on reduced 10% SDS-PAGE).

Summarizing the data for the competition studies is the following table:

| Immobilized Ligand | Hormone Spike-Back | Receptor Band |
|---|---|---|
| Inhibin A | None | +* |
| Inhibin A | Inhibin A | −** |
| Inhibin A | Activin A | not done |
| Activin A | None | + |
| Activin A | Inhibin A | + |
| Activin A | Activin A | − |

*"+" receptor band on SDS-PAGE
**"−" receptor band on SDS-PAGE competed.

EXAMPLE II

Inhibin/activin Receptor RNA Probes

A consensus N-terminal oligonucleotide was synthesized using standard DNA synthesis techniques to probe RNA slot blots. The sequence of this oligomer, which is based on the N-terminal sequence of the inhibin/activin receptor and uses mammalian-preferred codons, is as follows:

5'-TAATTCAGGTTTAGGAGTAGGAG-TAGGCATAATAATTTCAGTTTCTT-CAGTTAAAAC-3' (Sequence Identity No. 5)

An analysis of mRNA expression of the receptor sequence was done using Northern analysis. RNA was prepared from the tissues following homogenization in guanidine isothiocyanate, as described by Chomczynski and Sacchi, *Anal. Biochem.*, 162: 156-159 (1987). Poly(A)+ RNA was prepared from all sources by chromatography on an oligo(dT)-cellulose column. RNAs were electrophoresed on denaturing formaldehyde-agarose gels and the gels were stained with acridine orange to check for equivalent loading of RNA samples. RNA was transferred to nitrocellulose and hybridized using standard conditions for kinasing oligomers. Slot blots were made by dotting the various RNAs directly onto nitrocellulose and hybridizing directly. These methods are more fully described in Woodruff et al., *Molecular Endocrinol.*, 1: 561-568 (1987) and Woodruff et al., *Endocrinol.*, 128: 1647-1654 (1991).

The N-terminal consensus oligomer hybridized most intensely to bovine pituitary RNA and S6BC RNA (a mouse melanoma-derived cell line). It did not hybridize to TM4 +/− cAMP mRNA (mouse sertoli-derived cell line) or RL65 mRNA (mouse lung-cell derived cell line), as is clear from FIG. 4.

By Northern analysis, the mRNA species corresponding to the oligonucleotide is about 6.8 kb in size.

---

We claim:

1. An isolated activin receptor polypeptide which does not bind to TGF-$\beta$, has a molecular weight on reduced 10% SDS-PAGE of 135–150 Kd, and has an N-terminus of: ValLeuThrGluGluThrGluIleIleMet-ProThrProLysProGluLeuXaaAlaXaaXaaAsn, wherein Xaa indicates an unknown amino acid.

2. The polypeptide of claim 1 sharing at least 80% sequence identity with the mature human activin receptor polypeptide sequence.

3. The polypeptide of claim 1 that is mature human or bovine activin receptor.

4. An isolated antibody which binds to the polypeptide of claim 1.

* * * * *